US012763180B2

(12) United States Patent
Halperin et al.

(10) Patent No.: US 12,763,180 B2
(45) Date of Patent: Oct. 13, 2026

(54) METHODS, APPARATUSES AND COMPUTER PROGRAM PRODUCTS FOR GENERATING PREDICTED MULTI-DRUG CONTRAINDICATION DATA OBJECTS

(71) Applicant: UnitedHealth Group Incorporated, Minnetonka, MN (US)

(72) Inventors: Eran Halperin, Santa Monica, CA (US); Brian Hill, Culver City, CA (US); George Austin, Maplewood, NJ (US)

(73) Assignee: UNITEDHEALTH GROUP INCORPORATED, Minnetonka, MN (US)

( * ) Notice: Subject to any disclaimer, the term of this patent is extended or adjusted under 35 U.S.C. 154(b) by 449 days.

(21) Appl. No.: 18/052,508

(22) Filed: Nov. 3, 2022

(65) Prior Publication Data

US 2024/0153605 A1 May 9, 2024

(51) Int. Cl.
*G16H 20/10* (2018.01)
*G16H 10/60* (2018.01)
*G16H 70/40* (2018.01)

(52) U.S. Cl.
CPC ............ *G16H 20/10* (2018.01); *G16H 10/60* (2018.01); *G16H 70/40* (2018.01)

(58) Field of Classification Search
None
See application file for complete search history.

(56) References Cited

U.S. PATENT DOCUMENTS 9,305,267 B2 4/2016 Tatonetti et al.
10,769,242 B2 9/2020 Aronow et al.
(Continued)

FOREIGN PATENT DOCUMENTS

CN 116779094 A * 9/2023 ............. G16H 50/70
WO WO-2020226885 A1 * 11/2020 ............. A61B 5/361

OTHER PUBLICATIONS

Han, Ke, et al. "A review of approaches for predicting drug-drug interactions based on machine learning." Frontiers in pharmacology 12 (2022): 814858. (Year: 2022).*
(Continued)

*Primary Examiner* — Lena Najarian
(74) *Attorney, Agent, or Firm* — Alston & Bird LLP

(57) ABSTRACT

Methods, apparatuses, systems, computing devices, and/or the like are provided. An example method may generate a plurality of multidimensional patient-drug tensors based at least in part on a plurality of patient record data objects and a plurality of combined drug input vectors, generate an interaction-attentive prediction data object based at least in part on the plurality of multidimensional patient-drug tensors and at least one interaction-attentive machine learning model, generate an interaction-inattentive prediction data object based at least in part on the plurality of patient record data objects and an interaction-inattentive machine learning model, determine a drug combination indicator based at least in part on comparing the interaction-attentive prediction data object and the interaction-inattentive prediction data object, generate a predicted multi-drug contraindication data object based at least in part on the drug combination indicator, and perform one or more prediction-based actions.

17 Claims, 14 Drawing Sheets

(56) References Cited

U.S. PATENT DOCUMENTS

| | | | | |
|---|---|---|---|---|
| 11,120,913 | B2 | 9/2021 | Dey et al. | |
| 11,636,951 | B2 * | 4/2023 | Neumann | G06N 5/025 702/19 |
| 11,705,230 | B1 * | 7/2023 | Jain | G16H 20/10 705/3 |
| 2017/0116376 | A1 | 4/2017 | Fokoue-Nkoutche et al. | |
| 2017/0177803 | A1 * | 6/2017 | Hu | G16H 70/20 |
| 2020/0311613 | A1 * | 10/2020 | Ma | G06N 20/20 |
| 2021/0358637 | A1 | 11/2021 | Devdas | |
| 2023/0086217 | A1 * | 3/2023 | Hajij | G06N 3/08 705/3 |

OTHER PUBLICATIONS

"Drugs Interaction Checker," WebMD, (2 pages), [Retrieved from the Internet May 16, 2023] <URL: https://www.webmd.com/interaction-checker/default.htm>.

Abdullah, Sheikh S. et al. "Machine Learning For Identifying Medication-Associated Acute Kidney Injury," Informatics, vol. 7, No. 18, May 31, 2020, pp. 1-22, DOI: 10.3390/informatics7020018.

Christopoulou, Fenia et al. "Adverse Drug Events and Medication Relation Extraction In Electronic Health Records With Ensemble Deep Learning Methods," Journal of the American Medical Informatics Association, vol. 27, No. 1, Aug. 7, 2019, pp. 39-46, DOI: 10.1093/jamia/ocz101.

Dey, Sanjoy et al. "Predicting Adverse Drug Reactions Through Interpretable Deep Learning Framework," BMC Bioinformatics, vol. 19, Supplement 21:476, Jun. 10-12, 2018, pp. 1-13, DOI: 10.1186/s12859-018-2544-0.

Epocrates. "The #1 Mobile Medical Reference For Clinicians," (4 pages), (Year: 2020), [Retrieved from the Internet May 17, 2023] <URL: https://www.epocrates.com/features>.

Ernst, Frank R. et al. "Drug-Related Morbidity and Mortality: Updating The Cost-Of-Illness Model," Journal Of The American Pharmaceutical Association, vol. 41, No. 2, Mar./Apr. 2001, pp. 192-199, available online: https://citeseerx.ist.psu.edu/viewdoc/download?doi=10.1.1.469.2801&rep=rep1&type=pdf.

First Databank (FDB). "Drug-Disease Contraindications Module™", Drug Disase Contraindications Database, (Year: 2023), (5 pages), [Retrieved from the Internet May 17, 2023] <URL: https://www.fdbhealth.com/solutions/medknowledge-drug-database/medknowledge-clinical-modules/drug-disease-contraindications-module>.

Huang, Kexin et al. "MolTrans: Molecular Interaction Transformer For Drug-Target Interaction Prediction," Bioinformatics, vol. 37, Issue 6, pp. 830-836, Mar. 2021, (Advance Access Publication Date: Oct. 18, 2020), DOI: 10.1093/bioinformatics/btaa880.

Ianevski, Aleksandr et al. "SynergyFinder 2.0: Visual Analytics Of Multi-Drug Combination Synergies," Nucleic Acids Research, vol. 48, Web Server Issue, Mar. 25, 2020, (ePublished: Apr. 4, 2020), pp. W488-W493, DOI: 10.1093/nar/gkaa216.

Lin, Shenggeng et al. "MDF-SA-DDI: Predicting Drug-Drug Interaction Events Based On Multi-Source Drug Fusion, Multi-Source Feature Fusion and Transformer Self-Attention Mechanism," Briefings In Bioinformatics, vol. 23, Issue 1:bbab421, Oct. 20, 2021, (ePublished: Jan. 2022), pp. 1-13, DOI: 10.1093/bib/bbab421.

Lynch, Shalini S. "Drug Interactions," Clinical Pharmacology—Merck Manual Professional Version, Jul. 2022, (3 pages), University of California San Francisco School of Pharmacy, [Retrieved from the Internet May 16, 2023] <URL: https://www.merckmanuals.com/professional/clinical-pharmacology/factors-affecting-response-to-drugs/drug-interactions>.

Malone, Daniel C. et al. "Identification Of Serious Drug-Drug Interactions: Results Of The Partnership To Prevent Drug-Drug Interactions," Journal of the American Pharmacists Association, vol. 44, No. 2, pp. 142-151, Mar./Apr. 2004, available online: https://citeseerx.ist.psu.edu/viewdoc/download?doi=10.1.1.127.2395&rep=rep1&type=pdf.

Peng, Bo et al. "Deep Learning For High-Order Drug-Drug Interaction Prediction," In 10th ACM International Conference On Bioinformatics, Computational Biology and Health Informatics (ACM-BCB '19), pp. 197-206, Sep. 7-10, 2019, Niagara Falls, NY, USA, DOI: 10.1145/3307339.3342136.

* cited by examiner

400

| gene | CASP3 | CXCL8 | TNF | PTGS2 | IL1B | LINC00273 | BCL2 | APP | CYP3A4 | IL6 | ... |
|---|---|---|---|---|---|---|---|---|---|---|---|
| med_name | | | | | | | | | | | |
| SALBUTAMOL | 0.0 | 1.0 | 1.0 | 1.0 | 1.0 | 0.0 | -1.0 | 0.0 | 0.0 | 1.0 | ... |

Fig. 4

METHODS, APPARATUSES AND COMPUTER PROGRAM PRODUCTS FOR GENERATING PREDICTED MULTI-DRUG CONTRAINDICATION DATA OBJECTS

TECHNOLOGICAL FIELD

Embodiments of the present disclosure relate generally to predicting, estimating, and/or forecasting contraindications of multiple drugs when such drugs taken together by a patient. For example, various embodiments of the present disclosure may programmatically generate predicted multi-drug contraindication data objects.

BACKGROUND

A drug interaction may refer to a reaction between two (or more) drugs when they are taken or consumed by a user (such as a patient) at the same time or within a certain time period. A drug interaction may cause unexpected side effects such as contraindications, which can be harmful to the user/patient. For example, taking sedative medications and allergy medications together can slow the patient's reactions and make driving a car or operating machinery dangerous.

There are many technical challenges and difficulties associated with identifying combinations of drugs that can result in contraindications.

BRIEF SUMMARY

In general, embodiments of the present disclosure provide methods, apparatuses, systems, computing devices, computing entities, and/or the like.

In accordance with various embodiments of the present disclosure, an apparatus is provided. The apparatus may comprise at least one processor and at least one non-transitory memory comprising a computer program code. The at least one non-transitory memory and the computer program code may be configured to, with the at least one processor, cause the apparatus to generate a plurality of multidimensional patient-drug tensors based at least in part on a plurality of patient record data objects and a plurality of combined drug input vectors; generate an interaction-attentive prediction data object based at least in part on the plurality of multidimensional patient-drug tensors and at least one interaction-attentive machine learning model; generate an interaction-inattentive prediction data object based at least in part on the plurality of patient record data objects and an interaction-inattentive machine learning model; determine a drug combination indicator based at least in part on comparing the interaction-attentive prediction data object and the interaction-inattentive prediction data object; in response to determining that a predicted significance indicator associated with the drug combination indicator satisfies a significance threshold, generate a predicted multi-drug contraindication data object based at least in part on the drug combination indicator; and perform one or more prediction-based actions based at least in part on the predicted multi-drug contraindication data object.

In some embodiments, the at least one non-transitory memory and the computer program code are configured to, with the at least one processor, cause the apparatus to: generate a plurality of drug input vectors associated with a drug identifier indicator; and generate a combined drug input vector based at least in part on the plurality of drug input vectors, wherein the combined drug input vector is associated with the drug identifier indicator.

In some embodiments, the plurality of drug input vectors comprises one or more of a drug text vector associated with the drug identifier indicator, a drug-gene interaction vector associated with the drug identifier indicator, a molecular structure vector associated with the drug identifier indicator, a drug-drug interaction vector associated with the drug identifier indicator, or a drug-condition interaction vector associated with the drug identifier indicator.

In some embodiments, the at least one non-transitory memory and the computer program code are configured to, with the at least one processor, cause the apparatus to: generate a plurality of reduced drug input vectors based at least in part on the plurality of combined drug input vectors.

In some embodiments, each of the plurality of patient record data objects comprises one or more drug identifier indicators and a health outcome indicator that are associated with a patient identifier indicator.

In some embodiments, each of the plurality of multidimensional patient-drug tensors comprises a patient identity dimension, a drugs taken dimension, and a drug representation dimension.

In some embodiments, the at least one non-transitory memory and the computer program code are configured to, with the at least one processor, cause the apparatus to: generate the patient identity dimension and the drugs taken dimension based at least in part on the plurality of patient record data objects; and generate the drug representation dimension based at least in part on the plurality of combined drug input vectors.

In some embodiments, when generating the interaction-attentive prediction data object, the at least one non-transitory memory and the computer program code are configured to, with the at least one processor, cause the apparatus to: generate a plurality of encoded multidimensional tensors based at least in part on inputting the plurality of multidimensional patient-drug tensors to an interaction-attentive encoding machine learning model.

In some embodiments, the interaction-attentive encoding machine learning model comprises a multi-head attention encoder.

In some embodiments, the plurality of encoded multidimensional tensors comprises a plurality of attention score indicators associated with a plurality of drug identifier indicators.

In some embodiments, the interaction-attentive encoding machine learning model comprises at least one of a single-headed attention encoder, a feed-forward neural network, or a nearest neighbor model. In some embodiments, one or more interaction-attentive encoding machine learning models in accordance with some embodiments of the present disclosure may be associated with other model types that account for co-occurrence of drugs, such as, but not limited to, decision tree, random forest, polynomial regression, and/or the like.

In some embodiments, the at least one non-transitory memory and the computer program code are configured to, with the at least one processor, cause the apparatus to: generate the interaction-attentive prediction data object based at least in part on inputting the plurality of encoded multidimensional tensors to an interaction-attentive predicting machine learning model.

In some embodiments, the plurality of patient record data objects comprises a plurality of patient gender indicators and a plurality of patient age indicators.

In some embodiments, the interaction-attentive predicting machine learning model comprises a feed-forward neural network. In some embodiments, the feed-forward neural network comprises a plurality of neural network layers. In some embodiments, the plurality of neural network layers comprises a patient gender layer and a patient age layer.

In some embodiments, the interaction-attentive prediction data object comprises a plurality of patient identifier indicators and a plurality of interaction-attentive predicted outcome indicators. In some embodiments, each of the plurality of patient identifier indicators is associated with one of the plurality of interaction-attentive predicted outcome indicators.

In some embodiments, prior to generating the interaction-inattentive prediction data object, the at least one non-transitory memory and the computer program code are configured to, with the at least one processor, cause the apparatus to: retrieve a plurality of training patient record data objects comprising a plurality of patient condition indicators and a plurality of health outcome indicators; and generate the interaction-inattentive machine learning model based at least in part on the plurality of training patient record data objects.

In some embodiments, the at least one non-transitory memory and the computer program code are configured to, with the at least one processor, cause the apparatus to: generate the interaction-inattentive prediction data object based at least in part on inputting the plurality of patient record data objects to the interaction-inattentive machine learning model.

In some embodiments, the interaction-inattentive machine learning model comprises a logistic regression model.

In some embodiments, the interaction-inattentive prediction data object comprises a plurality of patient identifier indicators and a plurality of interaction-inattentive predicted outcome indicators. In some embodiments, each of the plurality of patient identifier indicators is associated with one of the plurality of interaction-inattentive predicted outcome indicators.

In some embodiments, when generating the drug combination indicator, the at least one non-transitory memory and the computer program code are configured to, with the at least one processor, cause the apparatus to: determine at least one patient identifier indicator that is associated with: (1) an interaction-attentive predicted outcome indicator, from the interaction-attentive prediction data object, indicating a predicted unfavorable health outcome and (2) an interaction-inattentive predicted outcome indicator, from the interaction-inattentive prediction data object, indicating a predicted favorable health outcome; and determine the drug combination indicator associated with the at least one patient identifier indicator based at least in part on the plurality of patient record data objects.

In some embodiments, the at least one non-transitory memory and the computer program code are configured to, with the at least one processor, cause the apparatus to: generate the predicted significance indicator based at least in part on providing the drug combination indicator, the interaction-attentive prediction data object, and the interaction-inattentive prediction data object to a significance predicting machine learning model; and determine whether the predicted significance indicator satisfies the significance threshold.

In accordance with various embodiments of the present disclosure, a computer-implemented method is provided. The computer-implemented method may comprise generating a plurality of multidimensional patient-drug tensors based at least in part on a plurality of patient record data objects and a plurality of combined drug input vectors; generating an interaction-attentive prediction data object based at least in part on the plurality of multidimensional patient-drug tensors and at least one interaction-attentive machine learning model; generating an interaction-inattentive prediction data object based at least in part on the plurality of patient record data objects and an interaction-inattentive machine learning model; determining a drug combination indicator based at least in part on comparing the interaction-attentive prediction data object and the interaction-inattentive prediction data object; in response to determining that a predicted significance indicator associated with the drug combination indicator satisfies a significance threshold, generating a predicted multi-drug contraindication data object based at least in part on the drug combination indicator; and performing one or more prediction-based actions based at least in part on the predicted multi-drug contraindication data object.

In accordance with various embodiments of the present disclosure, a computer program product is provided. The computer program product may comprise at least one non-transitory computer-readable storage medium having computer-readable program code portions stored therein. The computer-readable program code portions comprise an executable portion configured to generate a plurality of multidimensional patient-drug tensors based at least in part on a plurality of patient record data objects and a plurality of combined drug input vectors; generate an interaction-attentive prediction data object based at least in part on the plurality of multidimensional patient-drug tensors and at least one interaction-attentive machine learning model; generate an interaction-inattentive prediction data object based at least in part on the plurality of patient record data objects and an interaction-inattentive machine learning model; determine a drug combination indicator based at least in part on comparing the interaction-attentive prediction data object and the interaction-inattentive prediction data object; in response to determining that a predicted significance indicator associated with the drug combination indicator satisfies a significance threshold, generate a predicted multi-drug contraindication data object based at least in part on the drug combination indicator; and perform one or more prediction-based actions based at least in part on the predicted multi-drug contraindication data object.

The above summary is provided merely for purposes of summarizing some example embodiments to provide a basic understanding of some aspects of the disclosure. Accordingly, it will be appreciated that the above-described embodiments are merely examples. It will be appreciated that the scope of the disclosure encompasses many potential embodiments in addition to those here summarized, some of which will be further described below.

BRIEF DESCRIPTION OF THE SEVERAL VIEWS OF THE DRAWING(S)

Having thus described the disclosure in general terms, reference will now be made to the accompanying drawings, which are not necessarily drawn to scale, and wherein:

Figure 1:
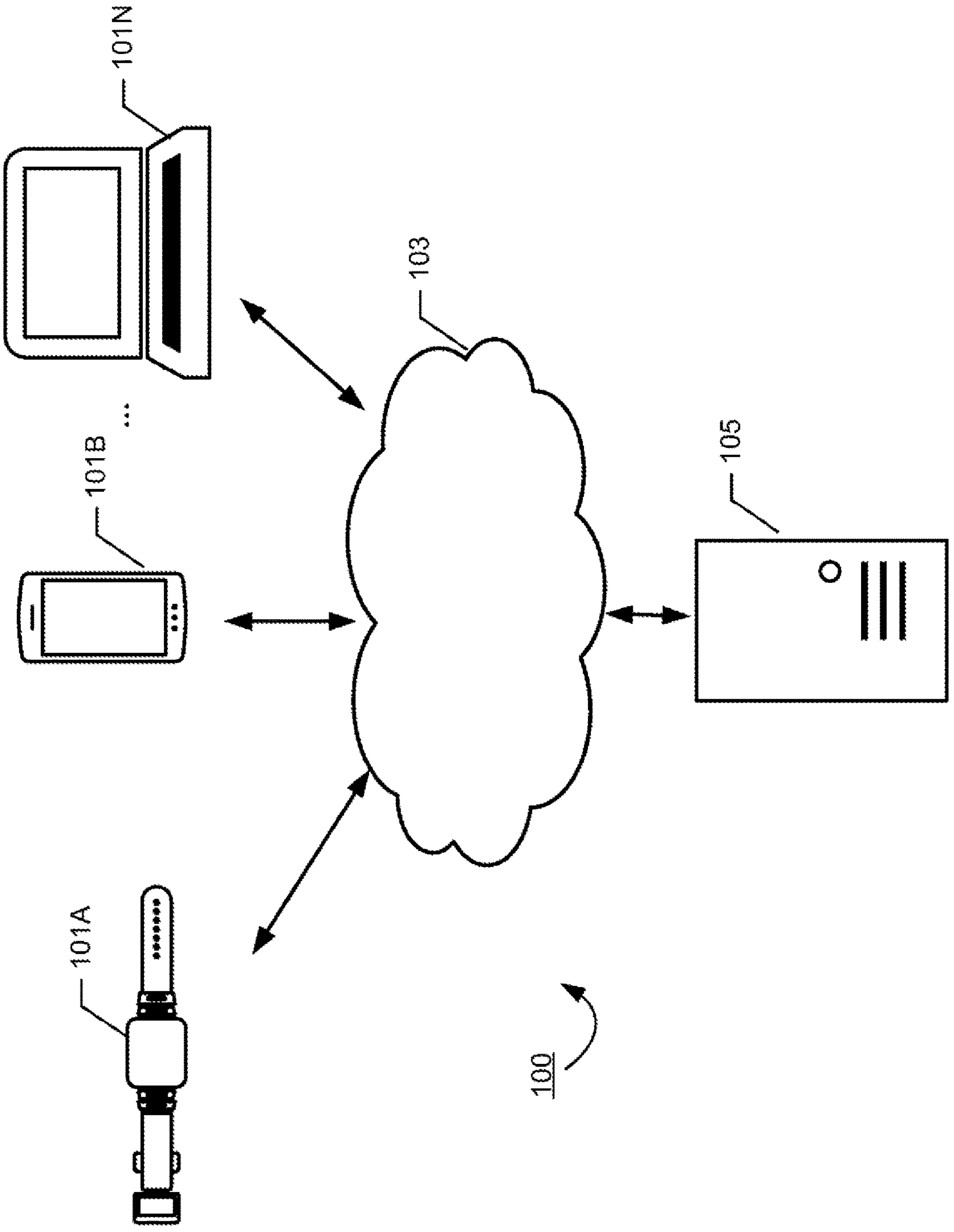
FIG. 1 is a diagram of an example multi-drug contraindication data object generation platform/system that can be used in accordance with various embodiments of the present disclosure.

FIG. 4, FIG. 5, FIG. 6A, FIG. 6B, FIG. 7, FIG. 8, FIG. 9, FIG. 10, FIG. 11, FIG. 12, and FIG. 13 provide example flowcharts and diagrams illustrating example steps, processes, procedures, and/or operations associated with an example multi-drug contraindication data object generation platform/system in accordance with various embodiments of the present disclosure.

DETAILED DESCRIPTION OF SOME EXAMPLE EMBODIMENTS

Various embodiments of the present disclosure now will be described more fully hereinafter with reference to the accompanying drawings, in which some, but not all embodiments of the disclosure are shown. Indeed, this disclosure may be embodied in many different forms and should not be construed as limited to the embodiments set forth herein; rather, these embodiments are provided so that this disclosure will satisfy applicable legal requirements. The term "or" (also designated as "/") is used herein in both the alternative and conjunctive sense, unless otherwise indicated. The terms "illustrative" and "exemplary" are used to be examples with no indication of quality level. Like numbers may refer to like elements throughout. The phrases "in one embodiment," "according to one embodiment," and/or the like generally mean that the particular feature, structure, or characteristic following the phrase may be included in at least one embodiment of the present disclosure and may be included in more than one embodiment of the present disclosure (importantly, such phrases do not necessarily may refer to the same embodiment).

I. COMPUTER PROGRAM PRODUCTS, METHODS, AND COMPUTING ENTITIES

Embodiments of the present disclosure may be implemented as computer program products that comprise articles of manufacture. Such computer program products may include one or more software components including, for example, applications, software objects, methods, data structures, and/or the like. A software component may be coded in any of a variety of programming languages. An illustrative programming language may be a lower-level programming language such as an assembly language associated with a particular hardware architecture and/or operating system platform/system. A software component comprising assembly language instructions may require conversion into executable machine code by an assembler prior to execution by the hardware architecture and/or platform/system. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

Additionally, or alternatively, embodiments of the present disclosure may be implemented as a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media may include all computer-readable media (including volatile and non-volatile media).

In one embodiment, a non-volatile computer-readable storage medium may include a floppy disk, flexible disk, hard disk, solid-state storage (SSS) (e.g., a solid-state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present disclosure may also be implemented as methods, apparatuses, systems, computing devices, computing entities, and/or the like. As such, embodiments of the present disclosure may take the form of a data structure, apparatus, system, computing device, computing entity, and/or the like executing instructions stored on a computer-readable storage medium to perform certain steps or operations. Thus, embodiments of the present disclosure may also take the form of an entirely hardware embodiment, an entirely computer program product embodiment, and/or an embodiment that comprises combination of computer program products and hardware performing certain steps or operations.

Embodiments of the present disclosure are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

II. EXEMPLARY SYSTEM ARCHITECTURE

FIG. 1 provides an illustration of a multi-drug contraindication data object generation platform/system 100 that can be used in conjunction with various embodiments of the present disclosure. As shown in FIG. 1, the multi-drug contraindication data object generation platform/system 100 may comprise apparatuses, devices, and components such as, but not limited to, one or more client computing entities 101A . . . 101N, one or more server computing entities 105 and one or more networks 103.

Each of the components of the multi-drug contraindication data object generation platform/system 100 may be in electronic communication with, for example, one another over the same or different wireless or wired networks 103 including, for example, a wired or wireless Personal Area Network (PAN), Local Area Network (LAN), Metropolitan Area Network (MAN), Wide Area Network (WAN), and/or the like. For example, the one or more client computing entities 101A . . . 101N and the one or more server computing entities 105 may be in electronic communication with one another to exchange data and information. Additionally, while FIG. 1 illustrates certain system entities as separate, standalone entities, the various embodiments are not limited to this particular architecture.

a. Exemplary Server Computing Entity

Figure 2:
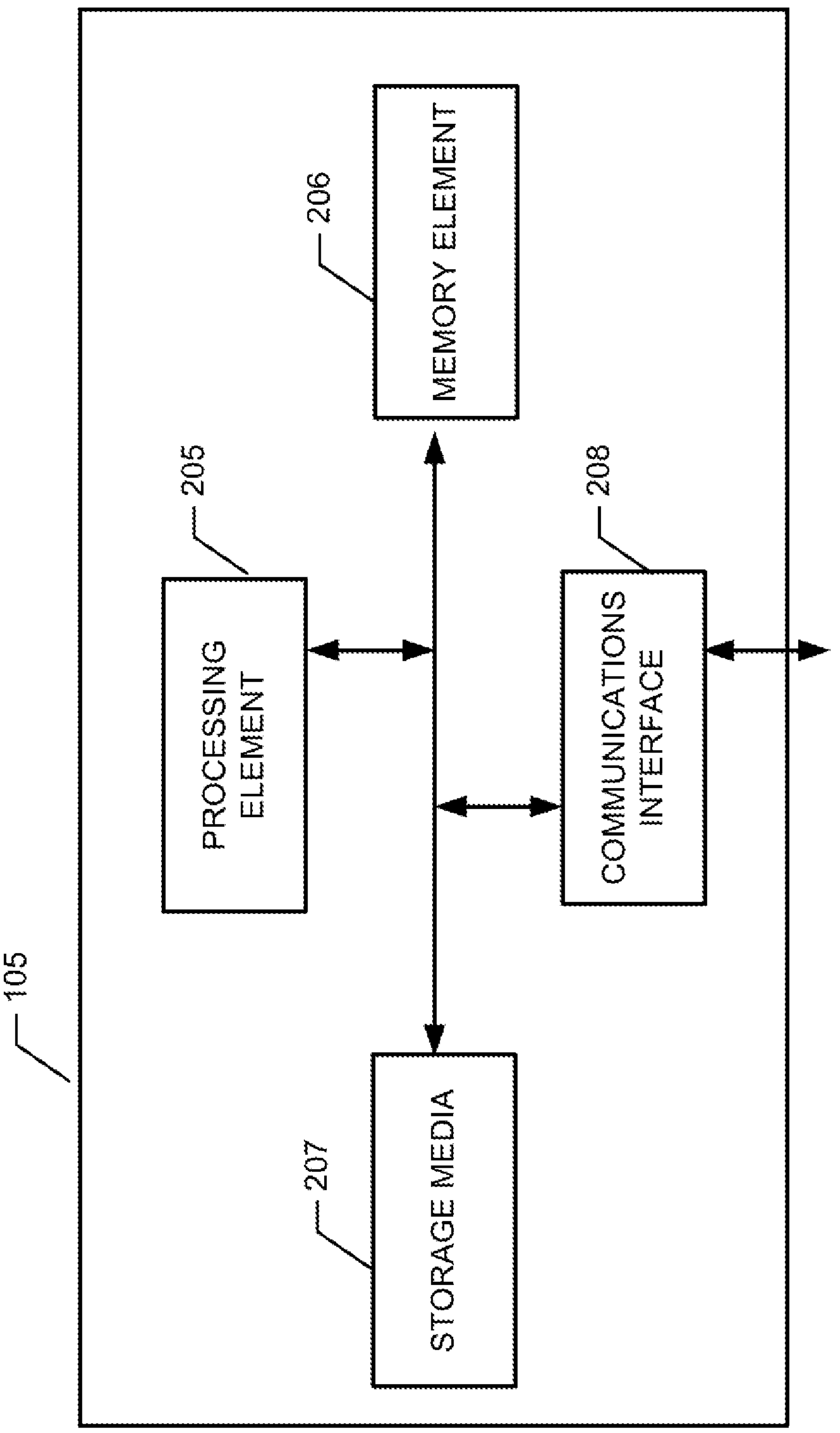
FIG. 2 is a schematic representation of an example server computing entity in accordance with various embodiments of the present disclosure.

FIG. 2 provides a schematic of a server computing entity 105 according to one embodiment of the present disclosure. In general, the terms computing entity, entity, device, system, and/or similar words used herein interchangeably may refer to, for example, one or more computers, computing entities, desktop computers, mobile phones, tablets, phablets, notebooks, laptops, distributed systems, items/devices, terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein. In one embodiment, these functions, operations, and/or processes can be performed on data, content, information, and/or similar terms used herein.

As indicated, in one embodiment, the server computing entity 105 may also include one or more network and/or communications interface 208 for communicating with various computing entities, such as by communicating data, content, information, and/or similar terms used herein that can be transmitted, received, operated on, processed, displayed, stored, and/or the like. For instance, the server computing entity 105 may communicate with other server computing entities 105, one or more client computing entities 101A, 101B, . . . 101N, and/or the like.

As shown in FIG. 2, in one embodiment, the server computing entity 105 may include or be in communication with one or more processing elements (for example, processing element 205) (also referred to as processors, processing circuitry, and/or similar terms used herein interchangeably) that communicate with other elements within the server computing entity 105 via a bus, for example, or network connection. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present disclosure when configured accordingly.

In one embodiment, the server computing entity 105 may further include or be in communication with volatile media (also referred to as volatile storage, memory, memory storage, memory circuitry and/or similar terms used herein interchangeably). In one embodiment, the volatile storage or memory may also include one or more memory element 206 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory element 206 may be used to store at least portions of the databases, database instances, database management system entities, data, applications, programs, program modules, scripts, source code, object code, byte code, compiled code, interpreted code, machine code, executable instructions, and/or the like being executed by, for example, the processing element 205 as shown in FIG. 2 and/or the processing element 308 as described in connection with FIG. 3. Thus, the databases, database instances, database management system entities, data, applications, programs, program modules, scripts, source code, object code, byte code, compiled code, interpreted code, machine code, executable instructions, and/or the like may be used to control certain aspects of the operation of the server computing entity 105 with the assistance of the processing element 205 and operating system.

In one embodiment, the server computing entity 105 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or storage media 207 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or storage media 207 may store databases, database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably and in a general sense to may refer to a structured or unstructured collection of information/data that is stored in a computer-readable storage medium.

Storage media 207 may also be embodied as a data storage device or devices, as a separate database server or servers, or as a combination of data storage devices and separate database servers. Further, in some embodiments, storage media 207 may be embodied as a distributed repository such that some of the stored information/data is stored centrally in a location within the system and other information/data is stored in one or more remote locations. Alternatively, in some embodiments, the distributed repository may be distributed over a plurality of remote storage locations only. An example of the embodiments contemplated herein would include a cloud data storage system maintained by a third-party provider and where some or all of the information/data required for the operation of the recovery system may be stored. Further, the information/data required for the operation of the recovery system may also be partially stored in the cloud data storage system and partially stored in a locally maintained data storage system. More specifically, storage media 207 may encompass one or more data stores configured to store information/data usable in certain embodiments.

As indicated, in one embodiment, the server computing entity 105 may also include one or more network and/or communications interface 208 for communicating with various computing entities, such as by communicating data, content, information, and/or similar terms used herein interchangeably that can be transmitted, received, operated on, processed, displayed, stored, and/or the like. For instance, the server computing entity 105 may communicate with computing entities or communication interfaces of other server computing entities 105, client computing entities 101A-101N, and/or the like.

As indicated, in one embodiment, the server computing entity 105 may also include one or more network and/or communications interface 208 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the server computing entity 105 may be configured to communicate via wireless external communication networks using any of a variety of protocols, such as general packet radio service (GPRS), Universal Mobile Telecommunications System (UMTS), Code Division Multiple Access 1900 (CDMA1900), CDMA1900 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), Institute of Electrical and Electronics Engineers (IEEE) 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol. The server computing entity 105 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

As will be appreciated, one or more of the server computing entity's components may be located remotely from components of other server computing entities 105, such as in a distributed system. Furthermore, one or more of the components may be aggregated and additional components performing functions described herein may be included in the server computing entity 105. Thus, the server computing entity 105 can be adapted to accommodate a variety of needs and circumstances.

b. Exemplary Client Computing Entity

Figure 3:
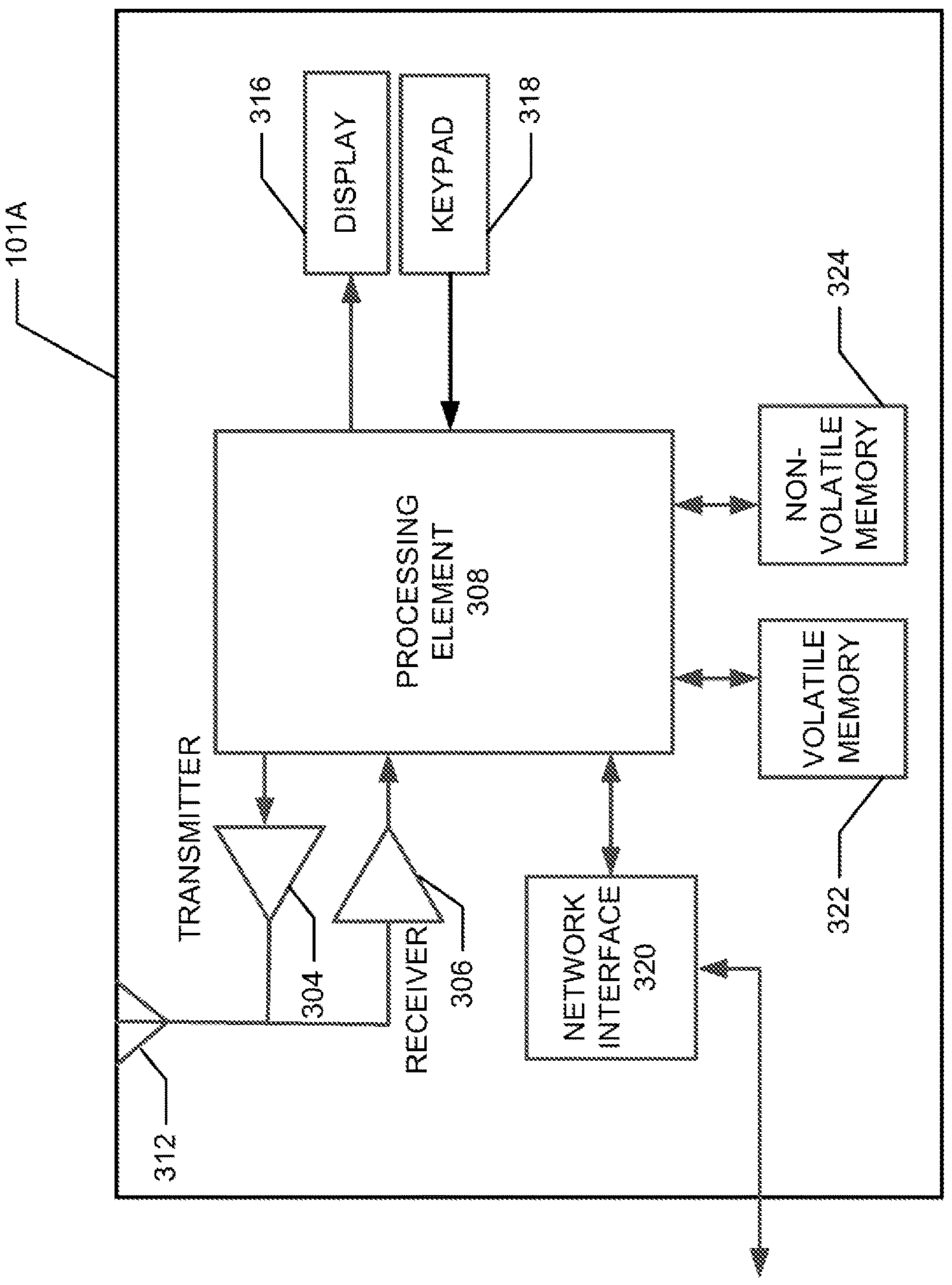
FIG. 3 is a schematic representation of an example client computing entity in accordance with various embodiments of the present disclosure.

FIG. 3 provides an illustrative schematic representative of one of the client computing entities 101A to 101N that can be used in conjunction with embodiments of the present disclosure. As will be recognized, the client computing entity may be operated by an agent and include components and features similar to those described in conjunction with the server computing entity 105. Further, as shown in FIG. 3, the client computing entity may include additional components and features. For example, the client computing entity 101A can include an antenna 312, a transmitter 304 (e.g., radio), a receiver 306 (e.g., radio), and a processing element 308 that provides signals to and receives signals from the transmitter 304 and receiver 306, respectively. The signals provided to and received from the transmitter 304 and the receiver 306, respectively, may include signaling information/data in accordance with an air interface standard of applicable wireless systems to communicate with various entities, such as a server computing entity 105, another client computing entity 101A, and/or the like. In this regard, the client computing entity 101A may be capable of operating with one or more air interface standards, communication protocols, modulation types, and access types. More particularly, the client computing entity 101A may comprise a network interface 320, and may operate in accordance with any of a number of wireless communication standards and protocols. In a particular embodiment, the client computing entity 101A may operate in accordance with multiple wireless communication standards and protocols, such as GPRS, UMTS, CDMA1900, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the client computing entity 101A can communicate with various other entities using Unstructured Supplementary Service data (USSD), Short Message Service (SMS), Multimedia Messaging Service (MMS), Dual-Tone Multi-Frequency (DTMF) Signaling, Subscriber Identity Module Dialer (SIM dialer), and/or the like. The client computing entity 101A can also download changes, add-ons, and updates, for instance, to its firmware, software (e.g., including executable instructions, applications, program modules), and operating system.

According to one embodiment, the client computing entity 101A may include location determining aspects, devices, modules, functionalities, and/or similar words used herein interchangeably. For example, the client computing entity 101A may include outdoor positioning aspects, such as a location module adapted to acquire, for example, latitude, longitude, altitude, geocode, course, direction, heading, speed, UTC, date, and/or various other information/data. In one embodiment, the location module can acquire data, sometimes known as ephemeris data, by identifying the number of satellites in view and the relative positions of those satellites. The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. Alternatively, the location information/data/data may be determined by triangulating the position in connection with a variety of other systems, including cellular towers, Wi-Fi access points, and/or the like. Similarly, the client computing entity 101A may include indoor positioning aspects, such as a location module adapted to acquire, for example, latitude, longitude, altitude, geocode, course, direction, heading, speed, time, date, and/or various other information/data. Some of the indoor aspects may use various position or location technologies including Radio-Frequency Identification (RFID) tags, indoor beacons or transmitters, Wi-Fi access points, cellular towers, nearby computing devices (e.g., smartphones, laptops) and/or the like. For instance, such technologies may include iBeacons, Gimbal proximity beacons, Bluetooth Low Energy (BLE) transmitters, Near Field Communication (NFC) transmitters, and/or the like. These indoor positioning aspects can be used in a variety of settings to determine the location of someone or something to within inches or centimeters.

The client computing entity 101A may also comprise a user interface comprising one or more user input/output interfaces (e.g., a display 316 and/or speaker/speaker driver coupled to a processing element 308 and a touch screen, keyboard, mouse, and/or microphone coupled to a processing element 308). For example, the user output interface may be configured to provide an application, browser, user interface, dashboard, webpage, and/or similar words used herein interchangeably executing on and/or accessible via the client computing entity 101A to cause display or audible presentation of information/data and for user interaction therewith via one or more user input interfaces. The user output interface may be updated dynamically from communication with the server computing entity 105. The user input interface can comprise any of a number of devices allowing the client computing entity 101A to receive data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the client computing entity 101A and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the client computing entity 101A can collect information/data, user interaction/input, and/or the like.

The client computing entity 101A can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, data, applications, programs, program modules, scripts, source code, object code, byte code, compiled code, interpreted code, machine code, executable instructions, and/or the like to implement the functions of the client computing entities 101A-101N.

c. Exemplary Networks

In one embodiment, the networks 103 may include, but are not limited to, any one or a combination of different types of suitable communications networks such as, for example, cable networks, public networks (e.g., the Internet), private networks (e.g., frame-relay networks), wireless networks, cellular networks, telephone networks (e.g., a public switched telephone network), or any other suitable private and/or public networks. Further, the networks 103 may have any suitable communication range associated therewith and may include, for example, global networks (e.g., the Internet), MANs, WANs, LANs, or PANs. In addition, the networks 103 may include medium over which network traffic may be carried including, but not limited to, coaxial cable, twisted-pair wire, optical fiber, a hybrid fiber coaxial (HFC) medium, microwave terrestrial transceivers, radio frequency communication mediums, satellite communication mediums, or any combination thereof, as well as a variety of network devices and computing platforms/systems provided by network providers or other entities.

Further, the networks 103 may utilize a variety of networking protocols including, but not limited to, TCP/IP based networking protocols. In some embodiments, the protocol is a custom protocol of JavaScript Object Notation (JSON) objects sent via a WebSocket channel. In some embodiments, the protocol is JSON over RPC, JSON over REST/HTTP, and/or the like.

III. EXEMPLARY OPERATION

Reference will now be made to FIG. 4, FIG. 5, FIG. 6A, FIG. 6B, FIG. 7, FIG. 8, FIG. 9, FIG. 10, FIG. 11, FIG. 12, and FIG. 13, which provide flowcharts and diagrams illustrating example steps, processes, procedures, and/or operations associated with an example multi-drug contraindication data object generation platform/system, an example client computing entity, and/or an example server computing entity in accordance with various embodiments of the present disclosure.

While example embodiments of the present disclosure may be described in the context of healthcare, a person of ordinary skill in the relevant technology will recognize that embodiments of the present disclosure are not limited to this context only.

a. Overview and Technical Advantages

In the United States, statistics show that one in five adults is concurrently prescribed five or more prescription drugs. However, the long-term health impacts of taking these drugs together are poorly understood. It is estimated that the annual cost due to adverse drug reactions within the United States is $30.1 billion, with up to $8,000 cost per patient experiencing adverse drug reactions. The overall cost of drug-related morbidity in the United States was estimated to be $177 billion in the year 2000, up from an estimated $77 billion in the year 1995.

There are many technical challenges and difficulties in identifying contraindications due to drug interactions between two or more drugs, particularly when the adverse health outcomes are long-term in nature.

For example, some systems for determining contraindicated drug combinations can identify only short-term impact of drug interactions (for example, when a patient has a heart attack after starting a new prescription) and cannot identify long-term impact of drug interactions.

As another example, some systems for determining contraindicated drug combinations can identify only contraindicated pairs of drugs by predicting pairwise drug interactions based at least in part on previously known interactions. These pairs of drugs usually have very high toxicity when combined (which leads to acute adverse health outcomes that are easy to identify), and/or have chemical components that are known to interact (and thus a clinical trial may be performed based at least in part on a hypothesis of interaction). Given the complex physiological effects of many drugs, it is likely that there are unknown pairs, triplets, quadruplets, or more numerous combinations of drugs that are harmful when taken in combination. However, identifying such combinations is difficult due to the great number of potentially confounding variables including patient demographics, health conditions, and large numbers of drugs taken concurrently. It is especially challenging to link such combinations to long-term health outcomes, as there is an even greater likelihood that complications from a specific set of drugs are confounded by other factors. As such, one of the primary obstacles in identifying harmful drug combinations from health data is the problem of how to identify cases in which bad health outcomes are caused by particular combinations of drugs as opposed to other factors.

Some machine learning models (such as logistic regression models) have the capacity to predict adverse health outcomes. However, such machine learning models tend to provide inaccurate estimates and predictions due to the large possible set of drugs that patients are prescribed, which can increase exponentially when there are triplets, quadruplets, or greater combinations of drugs. In addition, such machine learning models are not capable of distinguishing adverse health outcomes caused by drug interactions and adverse health outcomes caused by other factors.

Various embodiments of the present disclosure overcome the above-referenced technical challenges and difficulties and provide various technical improvements and advantages.

For example, various embodiments of the present disclosure identify the combination of laboratory measurements and pharmacy claims to identify drugs that drive harmful changes in organ function. Through this approach, various embodiments of the present disclosure provide a modeling structure that maps pharmacy claims to biologically relevant features of the claims' corresponding drugs (such as, but not limited to, their indications, gene interactions, and molecular/chemical structure). By comparing predictions between linear model(s) and model(s) driven by the biological features of drugs, various embodiments of the present disclosure identify sets of drugs whose contraindications are driven by underlying biological interactions. As such, various embodiments of the present disclosure apply machine learning based modeling to identify harmful combinations of drugs, which improves accuracy of predictions generated by machine learning models for identifying and preventing complications due to adverse drug effects from drug combinations.

As such, various embodiments of the present disclosure provide various technical advantages and improvements in computer technologies, including, but not limited to, improving accuracy of machine learning models in predicting multi-drug contraindications, additional details of which are described herein.

b. Definitions

In the present disclosure, the term "data object" may refer to a data structure that represents, indicates, stores and/or comprises data and/or information. In some embodiments, a data object may be in the form of one or more regions in one or more data storage devices (such as, but not limited to, a computer-readable storage medium) that comprise one or more values (such as, but not limited to, one or more identifiers, one or more metadata, and/or the like). In some embodiments, an example data object may comprise or be associated with one or more indicators, one or more metadata, and/or one or more other data objects.

In the present disclosure, the term "patient record data object" may refer to a type of data object that represents, indicates, stores and/or comprises data and/or information associated with a user of the multi-drug contraindication data object generation platform/system that includes, but not limited to, a patient.

For example, an example patient record data object indicates, comprises, represents, and/or is associated with one or more medical records associated with one or more patients. In some embodiments, an example patient record data object may be in the form of and/or comprise one or more electronic medical records ("EMRs") or electronic health records ("EHRs"), which indicates, comprises, represents, and/or is associated with data and information associated with one or more patients, such as, but not limited to, drugs (including, but not limited to, prescribed medications, antidotes, remedies, and/or the like) that the one or more patients are taking or consuming, current health statuses or conditions of the one or more patients (for example, any current symptoms that the one or more patients may exhibit or experience, any current medications that the one or more patients may be taking), testing results of the one or more patients (for example, but not limited to, blood tests, kidney tests, genetic tests, thyroid tests, and/or the like), health histories of the one or more patients (for example, any symptoms that the one or more patients may have exhibited or experienced in the past, any medications that the one or more patients may have taken in the past, any procedures that may have been conducted on the one or more patients, and/or the like), office visits of the one or more patients (for example, data and/or information associated with one or more visits to a doctor's office, a clinic, a pharmacy, a hospital, and/or the like for seeking medical help, medical treatment, medical assistance, pharmacy prescriptions, and/or the like), medical claims associated with the user, and/or the like.

In some embodiments, an example data object comprises one or more indicators. In the present disclosure, the term "indicator" may refer to a parameter, a data field, a data element, or the like that represents, indicates, stores and/or comprises an attribute of a data object.

In some embodiments, an example patient record data object comprises one or more indicators that include, but not limited to, one or more drug identifier indicators, one or more health outcome indicators, one or more patient identifier indicator, one or more patient age indicators, one or more patient gender indicator, and/or the like.

In the present disclosure, the term "patient identifier indicator" may refer to a type of indicator associated with a patient record data object that represents, indicates, stores and/or comprises an identifier of a user of the multi-drug contraindication data object generation platform/system (such as, but not limited to, a patient). In some embodiments, the patient identifier indicator may be in the form of text string(s), numerical character(s), alphabetical character(s), alphanumeric code(s), American Standard Code for Information Interchange (ASCII) character(s) and/or the like.

In the present disclosure, the term "drug identifier indicator" may refer to a type of indicator associated with a patient record data object that represents, indicates, stores and/or comprises one or more identifiers corresponding to one or more drugs (including, but not limited to, prescribed medications, antidotes, remedies, and/or the like) that the user takes and/or receives. In some embodiments, the drug identifier indicator may be in the form of text string(s), numerical character(s), alphabetical character(s), alphanumeric code(s), ASCII character(s), and/or the like.

In the present disclosure, the term "patient age indicator" may refer to a type of indicator associated with a patient record data object that represents, indicates, stores and/or comprises an indication of a current age of the user, a birthday of the user, and/or the like. In some embodiments, the patient age indicator may be in the form of text string(s), numerical character(s), alphabetical character(s), alphanumeric code(s), ASCII character(s), and/or the like.

In the present disclosure, the term "patient gender indicator" may refer to a type of indicator associated with a patient record data object that represents, indicates, stores and/or comprises an indication of a gender of the user, including, but not limited to, biological gender, gender identity, sexual orientation, and/or the like. In some embodiments, the patient gender indicator may be in the form of text string(s), numerical character(s), alphabetical character(s), alphanumeric code(s), ASCII character(s), and/or the like.

In the present disclosure, the term "patient condition indicator" may refer to a type of indicator associated with a patient record data object that represents, indicates, stores and/or comprises one or more indications associated with one or more health conditions of the patient.

For example, the patient condition indicator may indicate the presence or absence of a disease or symptoms associated with the disease. Additionally, or alternatively, the patient condition indicator may indicate progression or severity of a disease or symptoms associated with the disease. Additionally, or alternatively, the patient condition indicator may indicate other data and/or information associated with the health condition of the patient.

In some embodiments, the patient condition indicator may be in the form of text string(s), numerical character(s), alphabetical character(s), alphanumeric code(s), ASCII character(s), and/or the like.

In the present disclosure, the term "health outcome indicator" may refer to a type of indicator associated with a patient record data object that represents, indicates, stores and/or comprises one or more health levels/outcomes associated with one or more users, including, but not limited to, a long-term health level/outcome of the user, a short-term health level/outcome of the user, and/or the like. In some embodiments, the health outcome indicator may be in the form of text string(s), numerical character(s), alphabetical character(s), alphanumeric code(s), ASCII character(s), and/or the like.

In some embodiments, the health outcome indicator may indicate a positive, good, or favorable health outcome of the user. For example, the health outcome indicator may indicate that one or more clinical vitals (such as, but not limited to, blood pressure, body temperature, and/or the like) are at a healthy level and/or improving towards a healthy level. As another example, the health outcome indicator may indicate that one or more laboratory measurements/results (such as, but not limited to, creatinine measurements, albumin measurements, potassium measurements, and blood urea nitrogen (BUN) measurements) are predicted, forecasted, and/or estimated to be at a healthy level and/or have been improving towards a healthy level.

While the description above provides example data and/or information that indicates favorable health outcomes in an example health outcome indicator, it is noted that the scope of the present disclosure is not limited to the description above. In some examples, an example health outcome indicator may comprise data and/or information that indicate good or favorable health outcomes in addition to or in alternative of these examples above.

In some embodiments, the health outcome indicator may indicate a negative, bad, or unfavorable health outcome of the user. For example, the example health outcome may indicate that one or more clinical vitals (such as, but not limited to, blood pressure, body temperature, and/or the like) are at an unhealthy level and/or deteriorating towards an unhealthy level. As another example, the example health outcome indicator may indicate that one or more laboratory measurements/results (such as, but not limited to, creatinine measurements, albumin measurements, potassium measurements, and BUN measurements) are at an unhealthy level and/or deteriorating towards an unhealthy level.

While the description above provides example data and/or information that indicates unfavorable health outcomes in an example health outcome indicator, it is noted that the scope of the present disclosure is not limited to the description above. In some examples, an example health outcome indicator may comprise data and/or information that indicate unfavorable health outcomes in addition to or in alternative of these examples above.

In the present disclosure, the term "training patient record data object" may refer to a type of patient record data object that is used for training one or more machine learning models described herein. For example, an example training patient record data object in accordance with some embodiments of the present disclosure may comprise one or more drug identifier indicators, one or more health outcome indicators, one or more patient identifier indicator, one or more patient age indicators, one or more patient gender indicator, and/or the like, similar to those described above.

In the present disclosure, the term "vector" may refer to a type of data object that comprises one or more values in a vector space. In some embodiments, the one or more values of the vectors are associated with quantities, directions, and magnitudes. In the present disclosure, the term "vector" and "embedding" are used interchangeably.

In some embodiments, an example vector in accordance with some embodiments of the present disclosure is one-dimensional (also referred to as an array). In some embodiments, an example vector in accordance with some embodiments of the present disclosure is two-dimensional (also referred to as a matrix).

In the present disclosure, the term "input vector" may refer to a type of vector that is formatted as an input to one or more machine learning models described herein.

In the present disclosure, the term "drug input vector" may refer to a type of input vector that represents, indicates, stores and/or comprises one or more values that are associated with one or more drugs (including, but not limited to, prescribed medications, antidotes, remedies, and/or the like).

As described in further details herein, in various embodiments of the present disclosure, different combinations of drug input vectors may be used to yield some predictive value. For example, various embodiments of the present disclosure provide various types of drug input vectors that include, but are not limited to, drug text vectors, drug-gene interaction vectors, molecular structure vectors, drug-drug interaction vectors, drug-condition interaction vectors, and/or the like.

In the present disclosure, the term "drug text vector" may refer to a type of drug input vector that represents, indicates, stores and/or comprises values associated with textual information of a drug (including, but not limited to, one or more descriptions of the drug, one or more summaries of the drug, one or more medical facts associated with the drug, and/or the like).

Various embodiments of the present disclosure may generate one or more drug text vectors based at least in part on one or more machine learning models such as, but not limited, text encoding models (also referred to as text encoders).

As an example, an example drug text vector may be generated by one or more text encoding models that have been pre-trained on medical text (such as, but not limited to, Bidirectional Encoder Representations from Transformers for Biomedical Text Mining (BioBERT)). In such an example, the one or more text encoding models are used to encode text associated with each of the drugs being analyzed by the multi-drug contraindication data object generation platform/system. In some embodiments, the output(s) of the one or more text encoding models comprises a vector of specified length for each drug.

In some embodiments, the example drug text vector may be generated based at least in part on providing textual information to the one or more text encoding models. In some embodiments, textual information may come from a variety of sources such as, but not limited to, drug descriptions in medical reference materials, drug information/description in reference databases (e.g. medical databases, drug databases), and/or the like. In some embodiments, a computing entity may perform an automated internet search to gather textual information associated with each drug. Examples of reference databases that can provide drug information/description include, but are not limited to, DrugBank, Center Watch, DailyMed, and/or the like.

As illustrated in the examples above, example drug text vectors in accordance with some embodiments of the present disclosure can be natural language processing (NPL) based vectors. For example, NPL processing techniques can be implemented to generate drug text vectors. As described in detail herein, drug text vectors are implemented to search for and identify drug interactions.

In some embodiments, vector outputs generated based at least in part on text describing a drug can be more predictive than that of outputs generated from the name of a drug or numerical drug code alone. As an example, an example computing entity in accordance with some embodiments of the present disclosure may provide the following example textual information/texts associated with Omeprazole to one or more text encoding models:

"Omeprazole, according to the FDA label, is a proton pump inhibitor (PPI) used for the following purposes: Treatment of active duodenal ulcer in adults, . . . "

In such an example, the one or more text encoding models may generate an example drug text vector based at least in part on the above example textual information/texts, and the example drug text vector may be in the form of an example array as follows:

[−0.02, 0.08, −0.07, −0.05, −0.07, −0.01, 0.65, −0.23, −0.09, −0.41, 0.05, 0.34, −0.15, −0.39, −0.05, . . . ]

As such, drug text vectors in accordance with various embodiments of the present disclosure can provide technical benefits and advantages such as, but not limited to, improving accuracy in the prediction of multi-drug contraindications.

In the present disclosure, the term "drug-gene interaction vector" may refer to a type of drug input vector that represents, indicates, stores and/or comprises values associated with one or more known interactions between drugs and genes.

In some embodiments, an example drug-gene interaction vector is associated with or has a vector length that corresponds to a number of genes known to interact with the corresponding drug(s). As such, the vector length of the example drug-gene interaction can be set, limited, or determined based at least in part on the availability of data on drug-gene interactions and computing resources required to handle a certain length of vectors.

In various embodiments of the present disclosure, various different numerical representations can be implemented to represent various types of drug-gene interactions. Referring now to FIG. 4, an example numerical representation 400 of an example drug-gene interaction vector in accordance with some embodiments of the present disclosure is provided.

In the example shown in FIG. 4, the example numerical representation 400 is in a two-dimensional matrix format. In particular, the example numerical representation 400 is in a tabular format that comprises rows corresponding to columns. In some embodiments, each row corresponds to a drug, and each column corresponds to a gene.

In some embodiments, each digit (or column) in the example numerical representation 400 of the example drug-gene interaction vector encodes information associated with the interaction between the drug (that corresponds to the row) and a gene (that corresponds to the column). In the example shown in FIG. 4, each digit (or column) in the example numerical representation 400 of the example drug-gene interaction vector is assigned an integer with a value between 2 to −2. In such an example, the values 2 and −2 correspond to the efficacy of the drug relative to the condition that the drug is usually prescribed for treatment, with the value 2 indicating a synergistic treatment interaction and the value −2 indicating a deleterious treatment interaction. The values 1 and −1 correspond to the effect of the drug on gene expression, with the value 1 indicating increased gene expression and −1 indicating decreased gene expression. The value 0 corresponds to no known information indicating any interaction between the drug (that corresponds to the row) and the gene (that corresponds to the column).

While the description above provides an example numerical representation of an example drug-gene interaction vector, it is noted that the scope of the present disclosure is not limited to the description above. In some examples, an example drug-gene interaction vector may be in other forms or formats. For example, an example drug-gene interaction vector in various embodiments of the present disclosure may be in a form of a matrix that encodes drug-gene interactions and is different from the form shown in FIG. 4.

In some embodiments, drug-gene interaction vectors in accordance with some embodiments of the present disclosure are implemented in the context of deep learning. For example, the drug-gene interaction vectors can be provided into one or more machine learning models (such as, but not limited to, neural networks) to generate interaction-attentive predicted outcome indicators, details of which are described herein.

In the present disclosure, the term "molecular structure vector" may refer to a type of drug input vector that represents, indicates, stores and/or comprises values associated with a drug's structure of atoms and bonds between them. In other words, an example molecular structure vector is a vector representation of a drug's structure of atoms and bonds between them.

Figure 5:
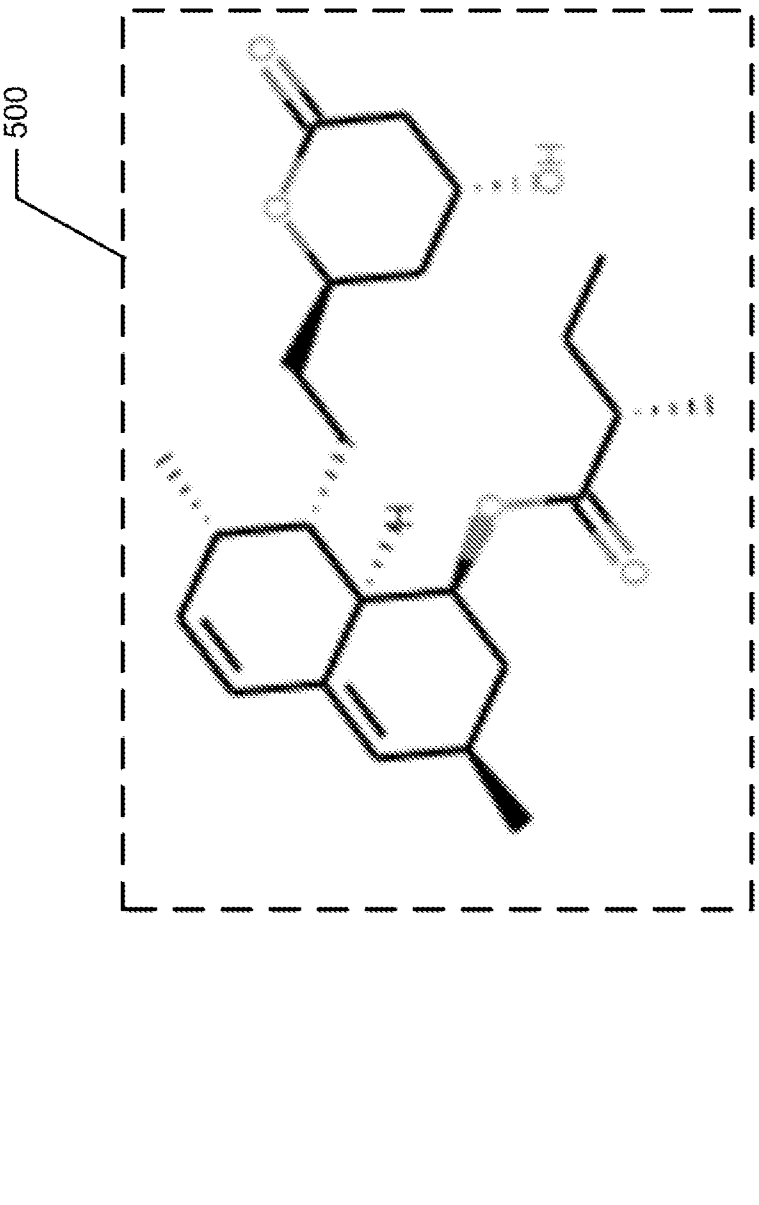

In some embodiments, a computing entity may generate a molecular structure vector for each drug associated with the multi-drug contraindication data object generation platform/system by implementing molecular contrastive learning of representations (MolCLR), and/or by citing external resources (such as, but not limited to, RDKit and PubChem) that can be used to match drug names to their chemicals. For example, MolCLR generates a molecular structure vector of 512 digits (columns). Referring now to FIG. 5, an example molecular structure representation 500 of Omeprazole is illustrated.

In some embodiments, a computing entity may generate the following example molecular structure vector in the form of an example array based at least in part on the example molecular structure representation 500 and MolCLR:

[0.0290, 0.7318, −0.9851, . . . , −0.8947, −−0.9415, −0.4380]

While the description above provides an example of generating an example molecular structure vector based at least in part on MolCLR, it is noted that the scope of the present disclosure is not limited to the description above. In some examples, an example method in accordance with some embodiments of the present disclosure may generate molecular structure vector(s) based at least in part on techniques in addition to or in alternative of MolCLR. In some embodiments, an example molecular structure vector may be associated with or has a vector length that is less than or more than 512 digits.

In the present disclosure, the term "drug-drug interaction vector" may refer to a type of drug input vector that represents, indicates, stores and/or comprises values associated with known interactions between drugs.

Similar to the example drug-gene interaction vectors described above, an example drug-drug interaction vector in accordance with some embodiments of the present disclosure may be in the form of numerical representations to express interactions between drugs numerically.

For example, an example drug-drug interaction vector may be in a two-dimensional matrix format. In some embodiments, the example drug-drug interaction vector is in a tabular format that comprises rows corresponding to columns. In some embodiments, each row corresponds to a drug, and each column also corresponds to a drug. In some embodiments, each digit in the example numerical representation of the example drug-drug interaction vector encodes information associated with the interaction between a drug (that corresponds to the row) and another drug (that corresponds to the column). In such an example, a negative digit in the numerical representation of the example drug-drug interaction vector denoting harmful interactions (for example, an interaction that contributed to or resulted in a favorable, positive, or good health outcome) and a positive digit in the numerical representation of the example drug-drug interaction vector denoting enhancing interactions (for example, an interaction that contributed to or resulted in an unfavorable, negative, or bad health outcome).

In the present disclosure, the term "drug-condition interaction vector" may refer to a type of drug input vector that represents, indicates, stores and/or comprises values associated with known interactions between drugs and health conditions. In some embodiments, the drug-condition interaction vector can be based at least in part on any way of representing a health condition, including, but not limited to, a specified list of diseases, International Classification of Diseases (ICD) ICD-10 codes, or phecodes. Additionally, or alternatively, a drug input vector representing each drug's side effects may be used to capture potential risks from a given drug.

In the present disclosure, the term "combined drug input vector" may refer to a type of drug input vector that combines multiple drug input vectors. For example, a computing entity in accordance with some embodiments of the present disclosure may receive a plurality of drug input vector that are associated with the same drug identifier indicator. In some embodiments, the computing entity appends each of the plurality of drug input vectors at the end of another drug input vector to generate the combined drug input vector.

While the description above provides an example of generating an example combined drug input vector, it is noted that the scope of the present disclosure is not limited to the description above. In some examples, an example combined drug input vector may be generated through one or more additional and/or alternative methods.

In some embodiments, the combined drug input vectors are provided as inputs to one or more machine learning models and/or inputs for generating multidimensional patient-drug tensors, details of which are described herein.

In the present disclosure, the term "reduced drug input vector" may refer to a type of drug input vector that has or is associated with a reduced vector length as compared to the vector length of the combined drug input vector.

For example, a computing entity in accordance with some embodiments of the present disclosure may generate one or more reduced drug input vectors based at least in part on combined drug input vectors through computing techniques such as, but not limited to, principal components analysis, auto-encoders, and/or the like.

In some embodiments, a reduced drug input vector can provide various technical benefits and improvements. For example, a drug input vector that is associated with a reduced vector length can provide technical benefits and advantages such as, but not limited to, substantially reduced computational costs and increased statistical power.

In the present disclosure, the term "multidimensional tensor" may refer to a type of data object that describes multidimensional relationships between dimensions of data objects in a vector space. For example, an example multidimensional tensor may comprise three dimensions. In such an example, each of the three dimensions comprises one or more data objects (such as, but not limited to, one or more vectors) that are mapped to one or more other data objects in other dimensions.

In the present disclosure, the term "multidimensional patient-drug tensor" may refer to a type of multidimensional tensor that describes multidimensional relationships among data/information associated with a user (for example, a patient) and data/information associated with one or more drugs (including, but not limited to, prescribed medications, antidotes, remedies, and/or the like). In some embodiments, an example multidimensional patient-drug tensor comprises three dimensions, including, but not limited to, a patient identity dimension, a drugs taken dimension, and a drug representation dimension.

In the present disclosure, the term "patient identity dimension" may refer to a dimension of an example multidimensional patient-drug tensor that comprises data and/or information associated with one or more users of the multi-drug contraindication data object generation platform/system (such as, but not limited to, one or more patients). In some embodiments, an example patient identity dimension of an example multidimensional patient-drug tensor may be generated based at least in part on patient record data objects, details of which are described herein.

In the present disclosure, the term "drugs taken dimension" may refer to a dimension of an example multidimensional patient-drug tensor that comprises data and/or information associated with one or more drugs (including, but not limited to, prescribed medications, antidotes, remedies, and/or the like) that the one or more users associated with the patient identity dimension of the corresponding example multidimensional patient-drug tensor are taking or consuming. In some embodiments, an example drugs taken dimension of an example multidimensional patient-drug tensor may be generated based at least in part on the patient record data objects, details of which are described herein.

In the present disclosure, the term "drug representation dimension" may refer to a dimension of an example multidimensional patient-drug tensor that comprises data and/or information associated with one or more drugs that are related to the drugs taken dimension of the corresponding example multidimensional patient-drug tensor. In some embodiments, an example drug representation dimension of an example multidimensional patient-drug tensor is generated based at least in part on a plurality of combined drug input vectors that are associated with the one or more drugs related to the drugs taken dimension of the corresponding example multidimensional patient-drug tensor, details of which are described herein.

In the present disclosure, the term "interaction-attentive prediction data object" may refer to a type of data object that represents, indicates, stores and/or comprises data and/or information associated with one or more predictions, estimates, and/or forecasts on one or more health outcomes associated with one or more users that are based at least in part on one or more interactions among drugs (including, but not limited to, prescribed medications, antidotes, remedies, and/or the like) that the one or more users are taking or consuming.

In some embodiments, an example interaction-attentive prediction data object comprises a plurality of patient identifier indicators and a plurality of interaction-attentive predicted outcome indicators. In some embodiments, each of the plurality of patient identifier indicators is associated with one of the plurality of interaction-attentive predicted outcome indicators.

In the present disclosure, the term "interaction-attentive predicted outcome indicator" may refer to a type of indicator associated with an interaction-attentive prediction data object that represents, indicates, stores and/or comprises predictions, estimates, and/or forecasts on one or more health levels/outcomes (including, but not limited to, long-term health level/outcomes, short-term health level/outcomes, and/or the like) associated with one or more users based at least in part on one or more interactions among drugs (including, but not limited to, prescribed medications, antidotes, remedies, and/or the like) that the one or more users are taking or consuming. In some embodiments, the interaction-attentive predicted outcome indicator may be in the form of text string(s), numerical character(s), alphabetical character(s), alphanumeric code(s), ASCII character(s), and/or the like.

In some embodiments, an example interaction-attentive predicted outcome indicator of an example interaction-attentive prediction data object may be in the form of a binary value that indicates either a predicted favorable health outcome or a predicted unfavorable health outcome. In some embodiments, an example interaction-attentive predicted outcome indicator of an example interaction-attentive prediction data object may indicate a likelihood of a predicted favorable health outcome. In some embodiments, an example interaction-attentive predicted outcome indicator of an example interaction-attentive prediction data object may indicate a likelihood of a predicted unfavorable health outcome.

While the description above provides example forms of interaction-attentive predicted outcome indicators, it is noted that the scope of the present disclosure is not limited to the description above. In some examples, an example interaction-attentive predicted outcome indicator may be in one or more additional and/or alternative forms.

In the present disclosure, when the example interaction-attentive predicted outcome indicator of an example interaction-attentive prediction data object indicates a predicted favorable health outcome, the example interaction-attentive prediction data object predicts, forecasts, and/or estimates an improvement in the health level/outcome associated with a user. For example, one or more clinical vitals (such as, but not limited to, blood pressure, body temperature, and/or the like) are predicted, forecasted, and/or estimated to be at a certain healthy level and/or have been improving towards a certain healthy level. As another example, one or more laboratory measurements/results (such as, but not limited to, creatinine measurements, albumin measurements, potassium measurements, and BUN measurements) are predicted, forecasted, and/or estimated to be at a certain healthy level and/or have been improving towards a certain healthy level.

While the description above provides examples of favorable health outcomes that are predicted, forecasted, and/or estimated by an example interaction-attentive prediction data object, it is noted that the scope of the present disclosure is not limited to the description above. In some examples, an example interaction-attentive prediction data object may predict, forecast, and/or estimate other favorable health outcomes in addition to or in alternative of these examples above.

In the present disclosure, when the example interaction-attentive predicted outcome indicator of an example interaction-attentive prediction data object indicates a predicted unfavorable health outcome, the example interaction-attentive prediction data object predicts, forecasts, and/or estimates a deterioration in the health level/outcome associated with a user. For example, one or more clinical vitals (such as, but not limited to, blood pressure, body temperature, and/or the like) are predicted, forecasted, and/or estimated to be at a certain unhealthy level and/or have been deteriorating towards a certain unhealthy level. As another example, one or more laboratory measurements/results (such as, but not limited to, creatinine measurements, albumin measurements, potassium measurements, and BUN measurements) are predicted, forecasted, and/or estimated to be at a certain unhealthy level and/or have been deteriorating towards a certain unhealthy level.

While the description above provides examples of unfavorable health outcomes that are predicted, forecasted, and/or estimated by an example interaction-attentive prediction data object, it is noted that the scope of the present disclosure is not limited to the description above. In some examples, an example interaction-attentive prediction data object may predict, forecast, and/or estimate other unfavorable health outcomes in addition to or in alternative of these examples above.

As described above, each of the plurality of patient identifier indicators in an example interaction-attentive prediction data object is associated with one of the plurality of interaction-attentive predicted outcome indicators. In some embodiments, each of the plurality of patient identifier indicators corresponds to or is mapped to one of the plurality of interaction-attentive predicted outcome indicators.

In some embodiments, an example interaction-attentive prediction data object may be in the form of a two-dimensional matrix. For example, the example interaction-attentive prediction data object comprises a plurality of rows and one or more columns. In some embodiments, each of the plurality of rows in the example interaction-attentive prediction data object corresponds to one of the plurality of patient identifier indicators. For example, the number of rows in the example interaction-attentive prediction data object corresponds to the number of patient identifier indicators.

As described above, interaction-attentive predicted outcome indicators of an example interaction-attentive prediction data object may be in one or more of a variety of forms. In some embodiments, the example interaction-attentive prediction data object may comprise one or more columns that correspond to the one or more forms of the interaction-attentive predicted outcome indicator. For example, an example interaction-attentive prediction data object may comprise a column corresponding to the interaction-attentive predicted outcome indicators indicating either a predicted favorable health outcome or a predicted unfavorable health outcome. Additionally, or alternatively, an example interaction-attentive prediction data object may comprise a column corresponding to the interaction-attentive predicted outcome indicators indicating a likelihood of a predicted favorable health outcome. Additionally, or alternatively, an example interaction-attentive prediction data object may comprise a column corresponding to the interaction-attentive predicted outcome indicators indicating a likelihood of a predicted unfavorable health outcome.

In the present disclose, the term "machine learning model" may refer to a computer model (that is embedded in, installed on, and/or executed by one or more computing entities) that is trained to generate one or more data objects, vectors, tensors, and/or the like as one or more outputs based at least in part on receiving one or more data objects, vectors, tensors, and/or the like as one or more inputs. As an example, an example machine learning model may be in the form of a computer-executable algorithm that is executed by a computing entity to improve the functionalities of the computing entity.

In the present disclosure, the term "interaction-attentive machine learning model" may refer to a type of machine learning model that generates data objects indicating one or more predictions, estimates, and/or forecasts based at least in part on, for example but not limited to, one or more interactions among drugs (including, but not limited to, prescribed medications, antidotes, remedies, and/or the like) that the one or more users are taking or consuming.

In accordance with various embodiments of the present disclosure, example interaction-attentive machine learning models may be associated with a variety of types, including, but not limited to, an interaction-attentive encoding machine learning model, an interaction-attentive predicting machine learning model, and/or the like.

In the present disclosure, the term "interaction-attentive encoding machine learning model" may refer to a type of interaction-attentive machine learning model that encodes multidimensional tensors including, but not limited to, multidimensional tensors. For example, an interaction-attentive encoding machine learning model may generate encoded multidimensional tensors as outputs in response to receiving multidimensional tensors (such as, but not limited to, multidimensional patient-drug tensors) as inputs.

In the present disclosure, the term "encoded multidimensional tensor" may refer to a type of multidimensional tensor that has been encoded by an interaction-attentive encoding machine learning model.

In accordance with some embodiments of the present disclosure, an example interaction-attentive encoding machine learning model may be in one or more of a variety of forms including, but not limited to, multi-head attention encoders, single-headed attention encoders, nearest neighbor models, and/or the like.

In the present disclosure, the term "multi-head attention encoder" may refer to a type of machine learning model that implements at least one multi-head attention mechanism in encoding one or more multidimensional tensors (such as, but not limited to, multidimensional patient-drug tensors).

As an example, the multi-head attention mechanism may cause data and/or information from different dimensions of the multidimensional tensor (such as, but not limited to, the patient identity dimension, the drugs taken dimension, and the drug representation dimension of the multidimensional patient-drug tensor) to run through attention functions of a multi-head attention encoder multiple times in parallel to transform and/or convert data and/or information into one or more attention vectors with attention scores measuring the strengths of relationships between the attention vectors.

In some embodiments, an encoded multidimensional tensor that is encoded by the multi-head attention encoder comprises attention score indicators associated with a plurality of drug identifier indicators. In the present disclosure, the term "attention score indicator" may refer to a type of indicator associated with an encoded multidimensional tensor that is encoded by the multi-head attention encoder and indicates one or more attention scores associated with data and/or information in one or more dimensions of the encoded multidimensional tensor. In some embodiments, the attention score indicator indicates the strengths of relationships between data and/or information in one or more dimensions of the encoded multidimensional tensor.

In the present disclosure, the term "single-headed attention encoder" may refer to a type of machine learning model that implements at least one single-head attention mechanism in encoding one or more multidimensional tensor (such as, but not limited to, multidimensional patient-drug tensors).

As an example, the single-head attention mechanism may cause data and/or information from different dimensions of the multidimensional tensor (such as, but not limited to, the patient identity dimension, the drugs taken dimension, and the drug representation dimension of the multidimensional patient-drug tensor) to run through attention functions of a single-head attention encoder one time to transform and/or convert data and/or information into one or more attention vectors.

In the present disclosure, the term "nearest neighbor model" may refer to a type of machine learning model that encodes one or more multidimensional tensors based at least in part on distance calculations between data and/or information in different dimensions of the multidimensional tensor. In some embodiments, an example nearest neighbor model may be in the form of K Nearest Neighbor (KNN).

In the present disclosure, the term "interaction-attentive predicting machine learning model" may refer to a type of interaction-attentive machine learning model that generates interaction-attentive prediction data objects as outputs based at least in part on receiving encoded multidimensional tensors as inputs.

In accordance with some embodiments of the present disclosure, an example interaction-attentive encoding machine learning model may be in one or more of a variety of forms, including, but not limited to, feed-forward neural networks. In some embodiments, one or more interaction-attentive encoding machine learning models in accordance with some embodiments of the present disclosure can be associated with other model types that account for co-occurrence of drugs, such as, but not limited to, decision tree, random forest, polynomial regression, and/or the like.

In the present disclosure, the term "feed-forward neural network" may refer to a type of machine learning model that comprises interconnected digital neurons that are organized into a plurality of neural network layers. In some embodiments, the feed-forward neural network is trained to generate one or more predictions, estimates, and/or forecasts on one or more health outcomes associated with one or more users.

In the present disclosure, the term "neural network layer" may refer to a collection of interconnected digital neurons that are formed together to receive one or more inputs and generate one or more outputs. In some embodiments, an example feed-forward neural network comprises a plurality of neural network layers that are associated with a plurality of neural network layer types.

For example, an example feed-forward neural network in accordance with some embodiments of the present disclosure may comprise a patient age layer. In the present disclosure, the term "patient age layer" may refer to a type of neural network layer that processes and/or analyzes data and/or information associated with the patient's age (such as, but not limited to, patient age indicators) from the encoded multidimensional tensors.

Additionally, or alternatively, an example feed-forward neural network in accordance with some embodiments of the present disclosure may comprise a patient gender layer. In the present disclosure, the term "patient gender layer" may refer to a type of neural network layer that processes and/or analyzes data and/or information associated with the patient's gender (such as, but not limited to, patient age indicators) from the encoded multidimensional tensors.

In the present disclosure, the term "interaction-inattentive prediction data object" may refer to a type of data object that represents, indicates, stores and/or comprises data and/or information associated with one or more predictions, estimates, and/or forecasts on one or more health outcomes associated with one or more users that are not based at least in part on interactions among drugs (including, but not limited to, prescribed medications, antidotes, remedies, and/or the like) that the one or more users are taking or consuming.

In some embodiments, an example interaction-inattentive prediction data object comprises a plurality of patient identifier indicators and a plurality of interaction-inattentive predicted outcome indicators. In some embodiments, each of the plurality of patient identifier indicators is associated with one of the plurality of interaction-inattentive predicted outcome indicators.

In the present disclosure, the term "interaction-inattentive predicted outcome indicator" may refer to a type of indicator associated with an interaction-inattentive prediction data object that represents, indicates, stores and/or comprises predictions, estimates, and/or forecasts on one or more health levels/outcomes (including, but not limited to, long-term health level/outcomes, short-term health level/outcomes, and/or the like) associated with one or more users that are not based at least in part on one or more interactions among drugs (including, but not limited to, prescribed medications, antidotes, remedies, and/or the like) that the one or more users are taking or consuming. In some embodiments, the interaction-inattentive predicted outcome indicator may be in the form of text string(s), numerical character(s), alphabetical character(s), alphanumeric code(s), ASCII character(s), and/or the like.

In some embodiments, an example interaction-inattentive predicted outcome indicator of an example interaction-inattentive prediction data object may be in the form of a binary value that indicates either a predicted favorable health outcome or a predicted unfavorable health outcome. In some embodiments, an example interaction-inattentive predicted outcome indicator of an example interaction-inattentive prediction data object may indicate a likelihood of a predicted favorable health outcome. In some embodiments, an example interaction-inattentive predicted outcome indicator of an example interaction-inattentive prediction data object may indicate a likelihood of a predicted unfavorable health outcome.

While the description above provides example forms of interaction-inattentive predicted outcome indicators, it is noted that the scope of the present disclosure is not limited to the description above. In some examples, an example interaction-inattentive predicted outcome indicator may be in one or more additional and/or alternative forms.

In the present disclosure, when the example interaction-inattentive predicted outcome indicator of an example interaction-inattentive prediction data object indicates a predicted favorable health outcome, the example interaction-inattentive prediction data object predicts, forecasts, and/or estimates an improvement in the health level/outcome associated with a user. For example, one or more clinical vitals (such as, but not limited to, blood pressure, body temperature, and/or the like) are predicted, forecasted, and/or estimated to be at a certain healthy level and/or have been improving towards a certain healthy level. As another example, one or more laboratory measurements/results (such as, but not limited to, creatinine measurements, albumin measurements, potassium measurements, and BUN measurements) are predicted, forecasted, and/or estimated to be at a certain healthy level and/or have been improving towards a certain healthy level.

While the description above provides examples of favorable health outcomes that are predicted, forecasted, and/or estimated by an example interaction-inattentive prediction data object, it is noted that the scope of the present disclosure is not limited to the description above. In some examples, an example interaction-inattentive prediction data object may predict, forecast, and/or estimate other favorable health outcomes in addition to or in alternative of these examples above.

In the present disclosure, when the example interaction-inattentive predicted outcome indicator of an example interaction-inattentive prediction data object indicates a predicted unfavorable health outcome, the example interaction-inattentive prediction data object predicts, forecasts, and/or estimates a deterioration in the health level/outcome associated with a user. For example, one or more clinical vitals (such as, but not limited to, blood pressure, body temperature, and/or the like) are predicted, forecasted, and/or estimated to be at a certain unhealthy level and/or have been deteriorating towards a certain unhealthy level. As another example, one or more laboratory measurements/results (such as, but not limited to, creatinine measurements, albumin measurements, potassium measurements, and BUN measurements) are predicted, forecasted, and/or estimated to be at a certain unhealthy level and/or have been deteriorating towards a certain unhealthy level.

While the description above provides examples of unfavorable health outcomes that are predicted, forecasted, and/or estimated by an example interaction-inattentive prediction data object, it is noted that the scope of the present disclosure is not limited to the description above. In some examples, an example interaction-inattentive prediction data object may predict, forecast, and/or estimate other unfavorable health outcomes in addition to or in alternative of these examples above.

As described above, each of the plurality of patient identifier indicators in an example interaction-inattentive prediction data object is associated with one of the plurality of interaction-inattentive predicted outcome indicators. In some embodiments, each of the plurality of patient identifier indicators corresponds to or is mapped to one of the plurality of interaction-inattentive predicted outcome indicators.

In some embodiments, an example interaction-inattentive prediction data object may be in the form of a two-dimensional matrix. For example, the example interaction-inattentive prediction data object comprises a plurality of rows and one or more columns. In some embodiments, each of the plurality of rows in the example interaction-inattentive prediction data object corresponds to one of the plurality of patient identifier indicators. For example, the number of rows in the example interaction-inattentive prediction data object corresponds to the number of patient identifier indicators.

As described above, interaction-inattentive predicted outcome indicators of an example interaction-inattentive prediction data object may be in one or more of a variety of forms. In some embodiments, the example interaction-inattentive prediction data object may comprise one or more columns that correspond to the one or more forms of the interaction-inattentive predicted outcome indicator. For example, an example interaction-inattentive prediction data object may comprise a column corresponding to the interaction-inattentive predicted outcome indicators indicating either a predicted favorable health outcome or a predicted unfavorable health outcome. Additionally, or alternatively, an example interaction-inattentive prediction data object may comprise a column corresponding to the interaction-inattentive predicted outcome indicators indicating a likelihood of a predicted favorable health outcome. Additionally, or alternatively, an example interaction-inattentive prediction data object may comprise a column corresponding to the interaction-inattentive predicted outcome indicators indicating a likelihood of a predicted unfavorable health outcome.

In the present disclosure, the term "interaction-inattentive machine learning model" may refer to a type of machine learning model that generates interaction-inattentive prediction data objects based at least in part on, for example but not limited to, patient record data objects, details of which are described herein.

In accordance with various embodiments of the present disclosure, an example interaction-inattentive machine learning model may be in one or more of a variety of forms including, but not limited to, logistic regression models.

In the present disclosure, the term "logistic regression model" may refer to a type of machine learning model that predicts, estimates, and/or forecasts the probability or likelihood of an event taking place. For example, the logistic regression model may generate predictions, estimates, and/or forecasts on one or more health levels/outcomes (including, but not limited to, long-term health level/outcomes, short-term health level/outcomes, and/or the like) associated with one or more users.

In the present disclosure, the term "predicted multi-drug contraindication data object" may refer to a type of data object that represents, indicates, stores and/or comprises data and/or information associated with a combination of two or more drugs that is predicted, estimated, and/or forecasted to at least partially cause, contribute to, and/or result in unfavorable health outcomes when the combination of two or more drugs are taken by a user (such as, but not limited to, a patient).

In the present disclosure, the term "drug combination indicator" may refer to a type of indicator that represents, indicates, stores and/or comprises two or more drug identifier indicators associated with two or more drugs that cause, contribute to, and/or result in predicted unfavorable health outcomes when such two or more drugs are taken and/or consumed together by a user (such as, but not limited, a patient).

In some embodiments, a drug combination indicator is associated with a predicted multi-drug contraindication data object. For example, a predicted multi-drug contraindication data object comprises a drug combination indicator. In such an example, the two or more drug identifier indicators of the drug combination indicator are associated with two or more drugs that are predicted, estimated, and/or forecasted to at least partially cause, contribute to, and/or result in unfavorable health outcomes when such two or more drugs are taken and/or consumed together by a user (such as, but not limited, a patient).

In some embodiments, the drug combination indicator may be in the form of text string(s), numerical character(s), alphabetical character(s), alphanumeric code(s), ASCII character(s), and/or the like.

In the present disclosure, the term "predicted significance indicator" may refer to a type of indicator associated with a drug combination indicator that represents, indicates, stores and/or comprises a predicted statistical significance value of the combination of two or more drugs (as indicated by the drug combination indicator) in at least partially causing or contributing to the predicted, estimated, and/or forecasted unfavorable health outcomes when the combination of two or more drugs are taken by a user (such as, but not limited to, a patient). In some embodiments, the predicted significance indicator may be in the form of text string(s), numerical character(s), alphabetical character(s), alphanumeric code(s), ASCII character(s), and/or the like.

In the present disclosure, the term "significance predicting machine learning model" may refer to a type of machine learning model that generates predicted significance indicators associated with the drug combination indicator. In some embodiments, the significance predicting machine learning model may implement statistical test techniques such as, but not limited to, chi-square test of statistical significance.

In the present disclosure, the term "significance threshold" may refer to a threshold value for comparison with a predicted statistical significance value associated with a combination of two or more drugs as described above. In some embodiments, when the predicted statistical significance value associated with the combination of two or more drugs satisfies the threshold value of the significance threshold, the two or more drugs are predicted, estimated, and/or forecasted to at least partially cause, contribute to, and/or result in unfavorable health outcomes when the combination of two or more drugs are taken by a user (such as, but not limited to, a patient). In some embodiments, when the predicted statistical significance value associated with the combination of two or more drugs does not satisfy the threshold value of the significance threshold, the two or more drugs are not predicted, estimated, and/or forecasted to cause, contribute to, and/or result in unfavorable health outcomes when the combination of two or more drugs are taken by a user (such as, but not limited to, a patient).

c. Exemplary Techniques for Generating Predicted Multi-Drug Contraindication Data Objects As described above, there are technical challenges, deficiencies and problems associated with generating computerized predictions on multi-drug contraindications, and various example embodiments of the present disclosure overcome such challenges. For example, referring now to FIG. 6A and FIG. 6B, an example method 600 of generating predicted multi-drug contraindication data objects in accordance with embodiments of the present disclosure is illustrated.

For example, the example method 600 may generate an interaction-inattentive prediction data object based at least in part on the plurality of patient record data objects and an interaction-inattentive machine learning model, generate an interaction-attentive prediction data object based at least in part on the plurality of multidimensional patient-drug tensors and at least one interaction-attentive machine learning model, and determine a drug combination indicator based at least in part on comparing the interaction-attentive prediction data object and the interaction-inattentive prediction data object. As such, the example method 600 may, for example, but not limited to, programmatically generate predictions on multi-drug contraindications with improved accuracy.

Figure 6A:
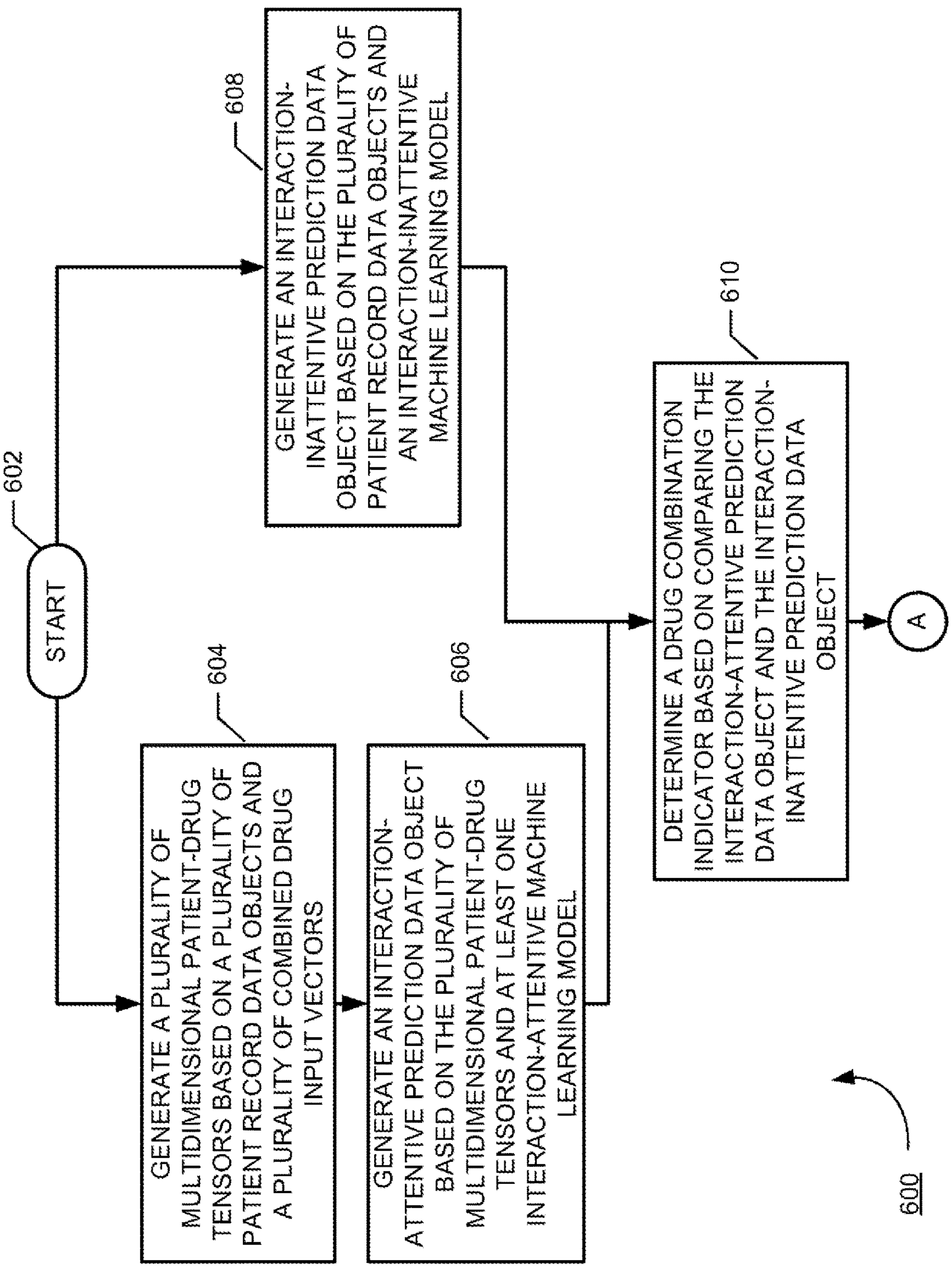

As shown in FIG. 6A, the example method 600 starts at step/operation 602. Subsequent to and/or in response to step/operation 602, the example method 600 proceeds to step/operation 604. At step/operation 604, a computing entity includes means (such as the processing element 205 of the server computing entity 105 described above in connection with FIG. 1 and FIG. 2 and/or the processing element 308 of the client computing entity 101A described above in connection with FIG. 1 and FIG. 3) to generate a plurality of multidimensional patient-drug tensors based at least in part on a plurality of patient record data objects and a plurality of combined drug input vectors.

As described above, an example multidimensional patient-drug tensor comprises a patient identity dimension that comprises data and/or information associated with one or more users of the multi-drug contraindication data object generation platform/system (such as, but not limited to, one or more patients). In some embodiments, the computing entity generates the patient identity dimension based at least in part on the plurality of patient record data objects.

In some embodiments, the plurality of patient record data objects comprises data and/or information that is potentially indicative of the users taking harmful combination(s) of drugs that result in unfavorable health outcomes. For example, the plurality of patient record data objects may comprise health outcome indicators. As described above, the health outcome indicators may comprise one or more laboratory measurements/results (such as, but not limited to, creatinine measurements, albumin measurements, potassium measurements, and BUN measurements). In some embodiments, the one or more laboratory measurements/results can be used to assess organ function levels (for example, by comparing or tracking the changes in laboratory measurements/results), which in turn can be used to determine whether the health outcomes are favorable outcomes or unfavorable outcomes. As such, in some embodiments, the example patient identity dimension of the example multidimensional patient-drug tensor may comprise the health outcome indicators of the patient record data objects.

As an example, the one or more laboratory measurements/results may comprise creatinine measurements, which can be used to assess function levels of the kidney. As illustrated in the example above, tracking changes in laboratory measurements/results allows various embodiments of the present disclosure to associate long-term drug use with long-term health outcomes, such as, but not limited to, how creatinine measurements change across a six-month period.

While the description above provides an example of tracking changes in laboratory measurements/results related to creatinine, it is noted that the scope of the present disclosure is not limited to the description above. In some embodiments, the patient identity dimension of the example multidimensional patient-drug tensor may additionally or alternatively comprise other data and/or information associated with the patient record data objects (such as measurements assessing health status of the users that include, but not limited to, albumin measurements, potassium measurements, and BUN measurements), other data from EMRs and/or EHRs associated with the one or more patients (such as, but not limited to, International Classification of Diseases (ICD) codes and Current Procedural Terminology (CPT) codes), and/or the like.

As described above, an example multidimensional patient-drug tensor comprises a drugs taken dimension. In some embodiments, the computing entity generates the drugs taken dimension based at least in part on the plurality of patient record data objects.

For example, the plurality of patient record data objects may comprise one or more drug identifier indicators associated with drugs (including, but not limited to, prescribed medications, antidotes, remedies, and/or the like) that the users take and/or receive. In some embodiments, the drugs taken dimension of the example multidimensional patient-drug tensor comprises one or more drug identifier indicators.

As described above, an example multidimensional patient-drug tensor comprises a drug representation dimension. In some embodiments, the computing entity generates the drug representation dimension based at least in part on the plurality of combined drug input vectors.

In some embodiments, the combined multiple drug input vectors combine multiple drug input vectors. In some embodiments, the computing entity generates the plurality of combined drug input vectors based at least in part on, for example but not limited to, the example method 800 in connection with FIG. 8, details of which are described herein.

Referring back to FIG. 6A, subsequent to and/or in response to step/operation 604, the example method 600 proceeds to step/operation 606. At step/operation 606, a computing entity includes means (such as the processing element 205 of the server computing entity 105 described above in connection with FIG. 1 and FIG. 2 and/or the processing element 308 of the client computing entity 101A described above in connection with FIG. 1 and FIG. 3) to generate an interaction-attentive prediction data object based at least in part on the plurality of multidimensional patient-drug tensors and at least one interaction-attentive machine learning model.

In some embodiments, the at least one interaction-attentive machine learning model comprises an interaction-attentive encoding machine learning model and an interaction-attentive predicting machine learning model. As described above, the interaction-attentive encoding machine learning model may refer to an interaction-attentive machine learning model that encodes multidimensional tensors, and the interaction-attentive predicting machine learning model may refer to an interaction-attentive machine learning model that predicts, estimates, and/or forecasts on one or more health outcomes associated with one or more users that are based at least in part on one or more interactions among drugs that the one or more users are taking or consuming.

In some embodiments, the computing entity provides the plurality of multidimensional patient-drug tensors as inputs to the interaction-attentive encoding machine learning model, and the interaction-attentive encoding machine learning model generates a plurality of encoded multidimensional tensors as outputs. Additional details are described herein, including, but not limited to, those described in connection with at least FIG. 10.

In some embodiments, the computing entity provides the plurality of encoded multidimensional tensors as inputs to the interaction-attentive predicting machine learning model, and the interaction-attentive predicting machine learning model generates a plurality of interaction-attentive prediction data objects as outputs. Additional details are described herein, including, but not limited to, those described in connection with at least FIG. 10.

Referring back to FIG. 6A, subsequent to and/or in response to step/operation 602, the example method 600 proceeds to step/operation 608. At step/operation 608, a computing entity includes means (such as the processing element 205 of the server computing entity 105 described above in connection with FIG. 1 and FIG. 2 and/or the processing element 308 of the client computing entity 101A described above in connection with FIG. 1 and FIG. 3) to generate an interaction-inattentive prediction data object based at least in part on the plurality of patient record data objects and an interaction-inattentive machine learning model.

As described above, the interaction-inattentive prediction data object predicts, estimates, and/or forecasts one or more health outcomes associated with one or more users without analyzing interactions among drugs (including, but not limited to, prescribed medications, antidotes, remedies, and/or the like) that the one or more users are taking or consuming. In some embodiments, the interaction-inattentive machine learning model generates the interaction-inattentive prediction data object as an output in response to receiving the plurality of patient record data objects as inputs. In some embodiments, the interaction-inattentive machine learning model may be in a variety of forms, including, but not limited to, a logistic regression model. Additional details associated with generating the interaction-inattentive prediction data object are described herein, including, but not limited to, those described in connection with at least FIG. 13.

Referring back to FIG. 6A, subsequent to and/or in response to step/operation 606 and step/operation 608, the example method 600 proceeds to step/operation 610. At step/operation 610, a computing entity includes means (such as the processing element 205 of the server computing entity 105 described above in connection with FIG. 1 and FIG. 2 and/or the processing element 308 of the client computing entity 101A described above in connection with FIG. 1 and FIG. 3) to determine a drug combination indicator based at least in part on comparing the interaction-attentive prediction data object and the interaction-inattentive prediction data object.

As described above, the interaction-attentive prediction data object predicts, estimates, and/or forecasts one or more health outcomes associated with one or more users based at least in part on one or more interactions among drugs (including, but not limited to, prescribed medications, antidotes, remedies, and/or the like) that the one or more users are taking or consuming.

For example, the interaction-attentive prediction data object may comprise a plurality of patient identifier indicators that are mapped to a plurality interaction-attentive predicted outcome indicators. In this example, each of the plurality interaction-attentive predicted outcome indicators indicates a predicted, estimated, and/or forecasted health level(s)/outcome(s) (including, but not limited to, long-term health level/outcomes, short-term health level/outcomes, and/or the like) associated with a user that is associated with one of the plurality of patient identifier indicators based at least in part on one or more interactions among drugs (including, but not limited to, prescribed medications, antidotes, remedies, and/or the like) that the user is taking or consuming.

As described above, the interaction-inattentive prediction data object predicts, estimates, and/or forecasts one or more health outcomes associated with one or more users not based at least in part on one or more interactions among drugs (including, but not limited to, prescribed medications, antidotes, remedies, and/or the like) that the one or more users are taking or consuming.

For example, the interaction-inattentive prediction data object may comprise a plurality of patient identifier indicators that are mapped to a plurality interaction-inattentive predicted outcome indicators. In this example, each of the plurality interaction-inattentive predicted outcome indicators indicates a predicted, estimated, and/or forecasted health level(s)/outcome(s) (including, but not limited to, long-term health level/outcomes, short-term health level/outcomes, and/or the like) of a user that is associated with one of the plurality of patient identifier indicators without considering interactions among drugs (including, but not limited to, prescribed medications, antidotes, remedies, and/or the like) that the user is taking or consuming.

As illustrated in the examples above, the health level(s)/outcome(s) (including, but not limited to, long-term health level/outcomes, short-term health level/outcomes, and/or the like) that are predicted, estimated, and/or forecasted by the interaction-attentive prediction data object are based at least in part on the one or more interactions among drugs (including, but not limited to, prescribed medications, antidotes, remedies, and/or the like) that the one or more users are taking or consuming. In contrast, the health level(s)/outcome(s) (including, but not limited to, long-term health level/outcomes, short-term health level/outcomes, and/or the like) that are predicted, estimated, and/or forecasted by the interaction-inattentive prediction data object are not based at least in part on the one or more interactions among drugs (including, but not limited to, prescribed medications, antidotes, remedies, and/or the like) that the one or more users are taking or consuming.

As such, if the health level(s)/outcome(s) associated with a patient identifier indicator that is predicted, estimated, and/or forecasted by the interaction-attentive prediction data object indicates a predicted unfavorable health outcome, but the health level(s)/outcome(s) associated with the same patient identifier indicator that is predicted, estimated, and/or forecasted by the interaction-inattentive prediction data object indicates a predicted favorable health outcome, the predicted unfavorable health outcome indicated by the interaction-attentive prediction data object is likely caused by the one or more interactions among drugs (including, but not limited to, prescribed medications, antidotes, remedies, and/or the like).

In some embodiments, the computing entity determines one or more patient identifier indicators that are associated with corresponding interaction-attentive predicted outcome indicators (from the interaction-attentive prediction data object) indicating predicted unfavorable health outcomes, and are also associated with corresponding interaction-inattentive predicted outcome indicators (from the interaction-inattentive prediction data object) indicating predicted favorable health outcomes. In some embodiments, the computing entity determines a plurality of drug identifier indicators that are associated with these one or more patient identifier indicators described above based at least in part on the patient record data objects.

In some embodiments, the computing entity determines the drug combination indicator based at least in part on the plurality of drug identifier indicators. For example, the computing entity identifies combinations of drug identifier indicators corresponding to drugs that are often taken by the one or more patients corresponding to the one or more patient identifier indicators described above.

In some embodiments, the drug combination indicator comprises a combination of two or more of the plurality of drug identifier indicators. For example, the drug combination indicator may comprise two drug identifier indicators ("a pair"). As another example, the drug combination indicator may comprise three drug identifier indicators ("a triple"). As another example, the drug combination indicator may comprise four drug identifier indicators ("a quadruplet"). As another example, the drug combination indicator may comprise more than four drug identifier indicators.

In some embodiments, the computing entity generates a plurality of drug combination indicators based at least in part on different combinations of two or more of the plurality of drug identifier indicators as described above.

Figure 6B:
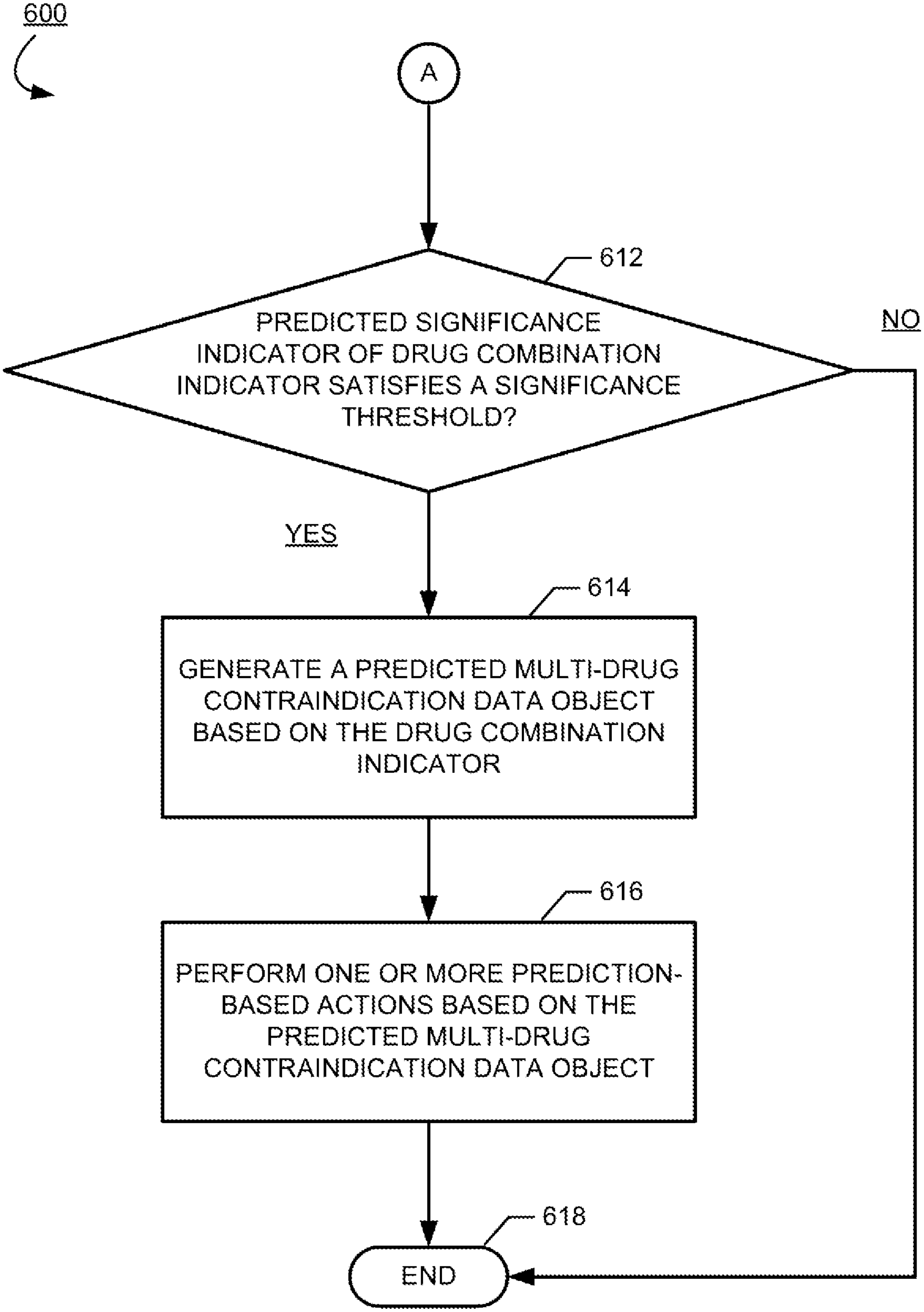

Referring back to FIG. 6A, subsequent to and/or in response to step/operation 610, the example method 600 proceeds to block A, which connects FIG. 6A to FIG. 6B.

Referring now to FIG. 6B, subsequent to and/or in response to block A (i.e., subsequent to and/or in response to step/operation 610), the example method 600 proceeds to step/operation 612. At step/operation 612, a computing entity includes means (such as the processing element 205 of the server computing entity 105 described above in connection with FIG. 1 and FIG. 2 and/or the processing element 308 of the client computing entity 101A described above in connection with FIG. 1 and FIG. 3) to determine whether a predicted significance indicator of the drug combination indicator satisfies a significance threshold.

As described above, the predicted significance indicator comprises a predicted statistical significance value associated with the drug combination indicator determined at step/operation 610. In some embodiments, the predicted statistical significance value indicates a predicted statistical significance value of the two or more drug identifier indicators that are identified by the drug combination indicator among the plurality of drug identifier indicators associated with the patient identifier indicators described above.

For example, based at least in part on comparing the interaction-attentive prediction data object and the interaction-inattentive prediction data object, the computing entity may determine a plurality of patient identifier indicators that are associated with predicted unfavorable health outcome based at least in part on the interaction-attentive prediction data object and are also associated with predicted favorable health outcome based at least in part on the interaction-inattentive prediction data object. In some embodiments, the computing entity determines a plurality of drug identifier indicators associated with the plurality of patient identifier indicators and generates a drug combination indicator based at least in part on a combination of two or more drug identifier indicators from the plurality of drug identifiers. As step/operation 612, the computing entity generates a predicted significant indicator indicating the statistical significance of the two or more drug identifier indicators among the plurality of drug identifiers.

In some embodiments, the computing entity provides the drug combination indicator and the plurality of drug identifier indicators to a significance predicting machine learning model as inputs, and the significance predicting machine learning model generates the predicted significant indicator as an output. In some embodiments, the significance predicting machine learning model may comprise one or more of a variety of statistical significance models. For example, the significance predicting machine learning model may implement the chi-square test. Additionally, or alternatively, the significance predicting machine learning model may implement the z-test. Additionally, or alternatively, the significance predicting machine learning model may implement the t-test. Additionally, or alternatively, the significance predicting machine learning model may implement other statistical tests.

As illustrated in the examples above, the predicted significance indicator indicates a predicted statistical significance that quantitatively indicates the strength of association between the two or more drug identifier indicators from a drug combination indicator and the predicted unfavorable health outcome indicated by the interaction-attentive predicted outcome indicator. In some embodiments, the computing entity determines a significance threshold that indicates a threshold level of statistical significance that is required for the drug combination indicator to be predicted, estimated, and/or forecasted to indicate a combination of drugs that at least partially contribute to or cause the predicted unfavorable health outcome.

As an example, the predicted significance indicator may comprise a predicted statistical significance value in the form of a p-value, which indicates the likelihood that the association between the drug combination indicator and the predicted unfavorable health outcome indicated by the interaction-attentive predicted outcome indicator is a product of chance. In this example, the significant threshold comprises a threshold p-value, and the computing entity compares the p-value from the predicted significance indicator with the threshold p-value. If the p-value from the predicted significance indicator is not more than the threshold p-value from the significant threshold, the computing entity determines that the predicted significance indicator of the drug combination indicator satisfies the significance threshold. If the p-value from the predicted significance indicator is more than the threshold p-value from the significant threshold, the computing entity determines that the predicted significance indicator of the drug combination indicator does not satisfy the significance threshold.

While the description above provides examples of predicted significance indicators and significance thresholds, it is noted that the scope of the present disclosure is not limited to the description above. In some examples, the computing entity may implement one or more additional or alternative types/values of predicted significance indicators and/or significance thresholds.

If, at step/operation 612, the computing entity determines that the predicted significance indicator of the drug combination indicator does not satisfy a significance threshold, the example method 600 proceeds to step/operation 618 and ends.

In other words, if the predicted significance indicator does not satisfy the significance threshold, the computing entity determines that the association between the drug identifier indicators from the drug combination indicator and the predicted unfavorable health outcome from the interaction-attentive predicted outcome indicator is due to chance and therefore not statistically significant.

If, at step/operation 612, the computing entity determines that the predicted significance indicator of the drug combination indicator satisfies the significance threshold, the example method 600 proceeds to step/operation 614. At step/operation 614, a computing entity includes means (such as the processing element 205 of the server computing entity 105 described above in connection with FIG. 1 and FIG. 2 and/or the processing element 308 of the client computing entity 101A described above in connection with FIG. 1 and FIG. 3) to generate a predicted multi-drug contraindication data object based at least in part on the drug combination indicator.

In some embodiments, in response to determining that the predicted significance indicator satisfies a significance threshold at step/operation 612, the computing entity generates a predicted multi-drug contraindication data object based at least in part on the drug combination indicator determined at step/operation 610. In some embodiments, the predicted multi-drug contraindication data object comprises the drug combination indicator determined at step/operation 610.

As described above, if the predicted significance indicator of the drug combination indicator is determined to satisfy the significance threshold at step/operation 612, the computing entity determines that the drug identifier indicators from the drug combination indicator are statistically significant. In other words, the drug identifier indicators are associated with drugs that are predicted, estimated, or forecasted to at least partially contribute to or cause the predicted unfavorable health outcome from the interaction-attentive prediction data object. As such, the computing entity determines that the drug combination indicator identifies a combination of drugs that are predicted, estimated, and/or forecasted to at least partially cause, contribute to, and/or result in predicted unfavorable health outcomes when the combination of drugs is taken by a user. In some embodiments, the computing entity generates the predicted multi-drug contraindication data object to include the drug combination indicator.

Referring back to FIG. 6B, subsequent to and/or in response to step/operation 614, the example method 600 proceeds to step/operation 616. At step/operation 616, a computing entity includes means (such as the processing element 205 of the server computing entity 105 described above in connection with FIG. 1 and FIG. 2 and/or the processing element 308 of the client computing entity 101A described above in connection with FIG. 1 and FIG. 3) to perform one or more prediction-based actions based at least in part on the predicted multi-drug contraindication data object.

In some embodiments, the computing entity may prospectively predict whether a combination of drugs can result in unfavorable health outcomes based at least in part on the predicted multi-drug contraindication data object.

For example, the computing entity may store the predicted multi-drug contraindication data object in a multi-drug contraindication data repository. In some embodiments, the computing entity may retrieve or receive a patient record data object that comprises a plurality of drug identifier indicators corresponding to a plurality of drugs that has been or will be prescribed to a patient. In some embodiments, the computing entity may determine whether a combination of two or more of the plurality of drug identifier indicators matches the drug combination indicator from the predicted multi-drug contraindication data object. If so, the computing entity determines that taking the combination of drugs together is predicted to be harmful to the patient and may, for example, generate and transmit an electronic message to a user computing device associated with the patient identifier indicator of the patient. In this example, the electronic message may comprise a warning to the patient that taking the combination of drugs together is predicted to be harmful.

While the description above provides an example of a prediction-based action, it is noted that the scope of the present disclosure is not limited to the description above. In some examples, an example computing entity may perform one or more additional and/or alternative prediction-based actions based at least in part on the predicted multi-drug contraindication data object.

Referring back to FIG. 6B, subsequent to and/or in response to step/operation 616, the example method 600 proceeds to step/operation 618 and ends.

As described above, there are technical challenges, deficiencies and problems associated with generating computerized predictions on multi-drug contraindications, and various example embodiments of the present disclosure overcome such challenges. For example, referring now to FIG. 7, an example method 700 of generating the predicted significance indicator in accordance with embodiments of the present disclosure is illustrated.

For example, the example method 700 may identify at least one patient identifier indicator associated with the interaction-attentive prediction data object and the interaction-inattentive prediction data object, determine the drug combination indicator associated with the at least one patient identifier indicator based at least in part on the plurality of patient record data objects, and generate the predicted significance indicator based at least in part on providing the drug combination indicator, the interaction-attentive prediction data object, and the interaction-inattentive prediction data object to a significance predicting machine learning model. As such, the example method 700 may, for example but not limited to, programmatically generate predictions on multi-drug contraindications with improved accuracy.

Figure 7:
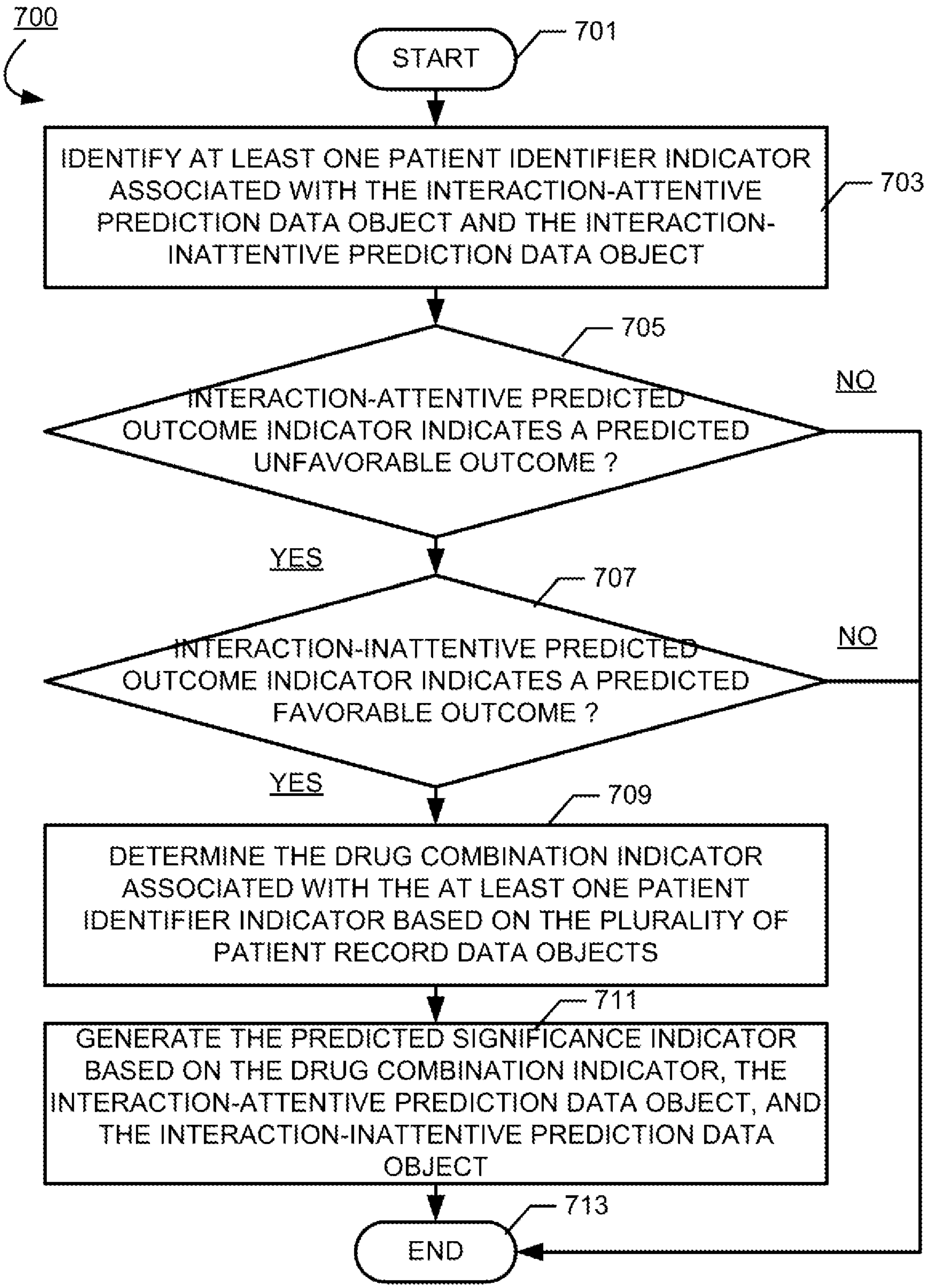

As shown in FIG. 7, the example method 700 starts at step/operation 701. Subsequent to and/or in response to step/operation 701, the example method 700 proceeds to step/operation 703. At step/operation 703, a computing entity includes means (such as the processing element 205 of the server computing entity 105 described above in connection with FIG. 1 and FIG. 2 and/or the processing element 308 of the client computing entity 101A described above in connection with FIG. 1 and FIG. 3) to identify at least one patient identifier indicator that is associated with the interaction-attentive prediction data object and the interaction-inattentive prediction data object.

As described above, the example interaction-attentive prediction data object comprises a plurality of patient identifier indicators and a plurality of interaction-attentive predicted outcome indicators, and the interaction-inattentive prediction data object comprises a plurality of patient identifier indicators and a plurality of interaction-inattentive predicted outcome indicators. In some embodiments, the computing entity identifies at least one patient identifier indicator that is associated with both the interaction-attentive prediction data object and the interaction-inattentive prediction data object. For example, the computing entity identifies at least one patient identifier indicator that is in both the interaction-attentive prediction data object and the interaction-inattentive prediction data object.

Referring back to FIG. 7, subsequent to and/or in response to step/operation 703, the example method 700 proceeds to step/operation 705. At step/operation 705, a computing entity includes means (such as the processing element 205 of the server computing entity 105 described above in connection with FIG. 1 and FIG. 2 and/or the processing element 308 of the client computing entity 101A described above in connection with FIG. 1 and FIG. 3) to determine whether the interaction-attentive predicted outcome indicator indicates a predicted unfavorable health outcome associated with the at least one patient identifier indicator identified at step/operation 703.

As described above, an example interaction-attentive prediction data object comprises a plurality of patient identifier indicators and a plurality of interaction-attentive predicted outcome indicators, and each of the plurality of patient identifier indicators is associated with one of the plurality of interaction-attentive predicted outcome indicators. In some embodiments, the computing entity identifies the interaction-attentive predicted outcome indicator that is associated with the at least one patient identifier indicator identified at step/operation 703, and determines whether the interaction-attentive predicted outcome indicator indicates a predicted unfavorable health outcome.

For example, an example interaction-attentive prediction data object may be in the form of a two-dimensional matrix. In such an example, the example interaction-attentive prediction data object comprises a plurality of rows and one or more columns. In some embodiments, each of the plurality of rows in the example interaction-attentive prediction data object corresponds to one of the plurality of patient identifier indicators. In some embodiments, each of the one or more columns corresponds to one type of the interaction-attentive predicted outcome indicators. For example, the example interaction-attentive prediction data object may comprise one column corresponding to the interaction-attentive predicted outcome indicator indicating a predicted favorable health outcome or a predicted unfavorable health outcome.

Continuing from the example above, the computing entity identifies the row in the example interaction-attentive prediction data object that corresponds to the at least one patient identifier indicator determined at step/operation 703, and determines whether the interaction-attentive predicted outcome indicator (from the column) associated with the row indicates a predicted favorable health outcome or a predicted unfavorable health outcome.

While the description above provides an example form of an interaction-attentive prediction data object, it is noted that the scope of the present disclosure is not limited to the description above. In some examples, an example interaction-attentive prediction data object may be in other formats.

If, at step/operation 705, the computing entity determines that the interaction-attentive predicted outcome indicator does not indicate a predicted unfavorable health outcome associated with the at least one patient identifier indicator, the example method 700 proceeds to step/operation 713 and ends.

If, at step/operation 705, the computing entity determines that the interaction-attentive predicted outcome indicator indicates a predicted unfavorable health outcome associated with the at least one patient identifier indicator, the example method 700 proceeds to step/operation 707. At step/operation 707, a computing entity includes means (such as the processing element 205 of the server computing entity 105 described above in connection with FIG. 1 and FIG. 2 and/or the processing element 308 of the client computing entity 101A described above in connection with FIG. 1 and FIG. 3) to determine whether the interaction-inattentive predicted outcome indicator indicates a predicted favorable health outcome associated with the at least one patient identifier indicator identified at step/operation 703.

As described above, an example interaction-inattentive prediction data object comprises a plurality of patient identifier indicators and a plurality of interaction-inattentive predicted outcome indicators, and each of the plurality of patient identifier indicators is associated with one of the plurality of interaction-inattentive predicted outcome indicators. In some embodiments, the computing entity identifies the interaction-inattentive predicted outcome indicator that is associated with the at least one patient identifier indicator identified at step/operation 703, and determines whether the interaction-attentive predicted outcome indicator indicates a predicted favorable health outcome.

For example, an example interaction-inattentive prediction data object may be in the form of a two-dimensional matrix. In such an example, the example interaction-inattentive prediction data object comprises a plurality of rows and one or more columns. In some embodiments, each of the plurality of rows in the example interaction-inattentive prediction data object corresponds to one of the plurality of patient identifier indicators. In some embodiments, each of the one or more columns corresponds to one type of the interaction-inattentive predicted outcome indicators. For example, the example interaction-inattentive prediction data object may comprise one column corresponding to the interaction-inattentive predicted outcome indicator indicating a predicted favorable health outcome or a predicted unfavorable health outcome.

Continuing from the example above, the computing entity identifies the row in the example interaction-inattentive prediction data object that corresponds to the at least one patient identifier indicator determined at step/operation 703, and determines whether the interaction-inattentive predicted outcome indicator (from the column) associated with the row indicates a predicted favorable health outcome or a predicted unfavorable health outcome.

While the description above provides an example form of an interaction-inattentive prediction data object, it is noted that the scope of the present disclosure is not limited to the description above. In some examples, an example interaction-inattentive prediction data object may be in other formats.

If, at step/operation 707, the computing entity determines that the interaction-inattentive predicted outcome indicator does not indicate a predicted favorable health outcome associated with the at least one patient identifier indicator, the example method 700 proceeds to step/operation 713 and ends.

If, at step/operation 707, the computing entity determines that the interaction-inattentive predicted outcome indicator indicates a predicted favorable health outcome associated with the at least one patient identifier indicator, the example method 700 proceeds to step/operation 709. At step/operation 709, a computing entity includes means (such as the processing element 205 of the server computing entity 105 described above in connection with FIG. 1 and FIG. 2 and/or the processing element 308 of the client computing entity 101A described above in connection with FIG. 1 and FIG. 3) to determine the drug combination indicator associated with the at least one patient identifier indicator based at least in part on the plurality of patient record data objects.

As illustrated above in connection with at least step/operation 703, step/operation 705, and step/operation 707, the computing entity determines at least one patient identifier indicator that is associated with:

(1) an interaction-attentive predicted outcome indicator, from the interaction-attentive prediction data object, indicating a predicted unfavorable health outcome and
(2) an interaction-inattentive predicted outcome indicator, from the interaction-inattentive prediction data object, indicating a predicted favorable health outcome.

As such, example embodiments of the present disclosure identify patients for whom at least one interaction-attentive machine learning model (such as, but not limited to, a combination of interaction-attentive encoding machine learning model and interaction-attentive predicting machine learning model) model correctly predicted an unfavorable health outcome and the interaction-inattentive machine learning model did not predict the unfavorable health outcome. The at least one interaction-attentive machine learning model encodes information representing interactions among drugs while the interaction-inattentive machine learning model does not encode information representing interactions among drugs. As such, if the at least one interaction-attentive machine learning model correctly predicts an unfavorable health outcome when the interaction-inattentive machine learning model does not predict an unfavorable health outcome, there is an increased likelihood that the cause of the unfavorable health outcome was due interactions between two or more drugs that the patients are taking.

As described above and in further details herein, in some embodiments, the at least one interaction-attentive machine learning model captures drug biology and interactions, while the interaction-inattentive machine learning model is driven solely by direct drug presence. By comparing the outputs from the two machine learning models, example embodiments of the present disclosure can identify potentially harmful drug interactions and/or the actual risk of the drug combination (for example, predictions outlining which drugs interactions are non-linear). As such, various embodiments of the present disclosure provide technical advantages and benefits of identifying contraindicated combinations that are greater in number than pairs (for example but not limited to, triplets, quadruplets, or more than quadruplets).

Referring back to FIG. 7, at step/operation 709, the computing entity determines the drug combination indicator associated with the at least one patient identifier indicator based at least in part on the plurality of patient record data objects.

As described above, the plurality of patient record data objects comprises a plurality of indicators that include, but not limited to, a plurality of patient identifier indicators and a plurality of drug identifier indicators. As an example, each of the plurality of patient record data objects is associated with a user of the multi-drug contraindication data object generation platform/system (for example, a patient). For example, each patient record data object comprises a patient identifier indicator and a plurality of drug identifier indicators that are associated with the drugs that the patient is taking or consuming.

As described above, step/operation 703, step/operation 705, and step/operation 707 of the example method 700 determines patient identifier indicators where the at least one interaction-attentive machine learning model generates an interaction-attentive predicted outcome indicator indicating a predicted unfavorable health outcome, and the interaction-inattentive machine learning model generates an interaction-inattentive predicted outcome indicator indicating a predicted favorable health outcome. In some embodiments, the computing entity retrieves one or more patient record data objects based at least in part on the patient identifier indicators, and determines drug identifier indicators from the one or more patient record data objects.

In some embodiments, the computing entity determines the drug combination indicator based at least in part on a combination of two or more drug identifier indicators. For example, the drug combination indicator comprises two drug identifier indicators from the drug identifier indicators. As another example, the drug combination indicator comprises three drug identifier indicators from the drug identifier indicators. As another example, the drug combination indicator comprises more than three drug identifier indicators from the drug identifier indicators.

Referring back to FIG. 7, subsequent to and/or in response to step/operation 709, the example method 700 proceeds to step/operation 711. At step/operation 711, a computing entity includes means (such as the processing element 205 of the server computing entity 105 described above in connection with FIG. 1 and FIG. 2 and/or the processing element 308 of the client computing entity 101A described above in connection with FIG. 1 and FIG. 3) to generate the predicted significance indicator based at least in part on the drug combination indicator, the interaction-attentive prediction data object, and the interaction-inattentive prediction data object.

As described above, the predicted significance indicator comprises a predicted statistical significance value of the combination of two or more drugs. In some embodiments, the predicted statistical significance value indicates a predicted statistical significance level of drug identifier indicators (from the drug combination indicator) among all the drug identifier indicators that are associated with the patient identifier indicators determined at step/operation 709.

In some embodiments, the computing entity provides the drug combination indicator, the interaction-attentive prediction data object, and the interaction-inattentive prediction data object to a significance predicting machine learning model as inputs, and the significance predicting machine learning model generates the predicted significance indicator as an output.

For example, the significance predicting machine learning model determines the predicted significance indicator based at least in part on calculating the predicted statistical significance value (such as, but not limited to, a p-value) that indicates how statistically significant the two or more drug identifier indicators from the drug combination indicator are among the drug identifier indicators associated with the at least one patient identifier indicator that is determined at step/operation 709.

Referring now to TABLE 1 below, an example of a statistical significance analysis in accordance with some embodiments of the present disclosure is illustrated.

TABLE 1

EXAMPLE STATISTICAL SIGNIFICANCE ANALYSIS

| DRUG COMBINATION INDICATOR | NUMBER OF PREDICTED UNFAVORABLE HEALTH OUTCOMES BASED AT LEAST IN PART ON THE INTERACTION-ATTENTIVE PREDICTION DATA OBJECT | NUMBER OF PREDICTED UNFAVORABLE HEALTH OUTCOMES BASED AT LEAST IN PART ON THE INTERACTION-INATTENTIVE PREDICTION DATA OBJECT |
|---|---|---|
| ATORVASTATIN CALCIUM - AMLODIPINE BESYLATE - SERTRALINE HCL | 2 | 10 |
| ATORVASTATIN CALCIUM - LEVOTHYROXINE SODIUM - METFORMIN HCL | 28 | 44 |
| ATORVASTATIN CALCIUM - METFORMIN HCL - SERTRALINE HCL | 4 | 19 |
| ATORVASTATIN CALCIUM - METFORMIN HCL - TIZANIDINE HCL | 12 | 26 |
| ATORVASTATIN CALCIUM - METFORMIN HCL - BENAZEPRIL HCL | 4 | 14 |
| ATORVASTATIN CALCIUM - SERTRALINE HCL - TIZANIDINE HCL | 0 | 13 |
| LEVOTHYROXINE SODIUM - METFORMIN HCL - SERTRALINE HCL | 0 | 8 |
| METFORMIN HCL - LOSARTAN POTASSIUM - SERTRALINE HCL | 0 | 7 |
| METFORMIN HCL - GLIPIZIDE - SERTRALINE HCL | 1 | 9 |

In the example statistical significance analysis shown above, the significance predicting machine learning model determines drug combination indicators based at least in part on the patient identifier indicators that is described in connection with step/operation 709, as reflected in the DRUG COMBINATION INDICATOR column in TABLE 1 above.

In some embodiments, the significance predicting machine learning model further determines the patient identifier indicators from the interaction-attentive prediction data object that are associated with each drug combination indicator, and determines the number of predicted unfavorable health outcomes (indicated by the interaction-attentive predicted outcome indicators from the interaction-attentive prediction data object) that are associated with these patient identifier indicators. In some embodiments, the computing entity provides the number in the NUMBER OF PREDICTED UNFAVORABLE HEALTH OUTCOMES BASED AT LEAST IN PART ON THE INTERACTION-ATTENTIVE PREDICTION DATA OBJECT column in TABLE 1 above.

In some embodiments, the significance predicting machine learning model further determines the patient identifier indicators from the interaction-inattentive prediction data object that are associated with each drug combination indicator, and determines the number of predicted unfavorable health outcomes (indicated by the interaction-inattentive predicted outcome indicators from the interaction-inattentive prediction data object) that are associated with these patient identifier indicators. In some embodiments, the computing entity provides the number in the NUMBER OF PREDICTED UNFAVORABLE HEALTH OUTCOMES BASED AT LEAST IN PART ON THE INTERACTION-INATTENTIVE PREDICTION DATA OBJECT column in TABLE 1 above.

In some embodiments, for each drug combination indicator, the significance predicting machine learning model compares the number of predicted unfavorable health outcomes based at least in part on the interaction-attentive prediction data object and the number of predicted unfavorable health outcomes based at least in part on the interaction-inattentive prediction data object. The bigger the difference between the two numbers, the more likely that the predicted unfavorable health outcome is at least partially caused by the combination of drugs indicated by the drug combination indicator, and therefore the higher the predicted statistical significance value of the predicted significance indicator associated with the drug combination indicator.

As an example, the difference between the number of predicted unfavorable health outcomes based at least in part on the interaction-attentive prediction data object and the number of predicted unfavorable health outcomes based at least in part on the interaction-inattentive prediction data object for "ATORVASTATIN CALCIUM-SERTRALINE HCL-TIZANIDINE HCL" is 13. The difference between the number of predicted unfavorable health outcomes based at least in part on the interaction-attentive prediction data object and the number of predicted unfavorable health outcomes based at least in part on the interaction-inattentive prediction data object for "METFORMIN HCL-GLIPIZIDE-SERTRALINE HCL" is 8. In this example, the computing entity determines that the predicted statistical significance value for "ATORVASTATIN CALCIUM-SERTRALINE HCL-TIZANIDINE HCL" is higher than the predicted statistical significance value for "METFORMIN HCL-GLIPIZIDE-SERTRALINE HCL."

In some embodiments, subsequent to generating the predicted significance indicator, the computing entity determines whether the predicted significance indicator satisfies the significance threshold, similar to those described above in connection with at least step/operation 612 of FIG. 6B.

Referring back to FIG. 7, subsequent to and/or in response to step/operation 711, the example method 700 proceeds to step/operation 713 and ends.

d. Exemplary Techniques for Generating Multidimensional Patient-Drug Tensors As described above, there are technical challenges, deficiencies and problems associated with generating computerized predictions on multi-drug contraindications, and various example embodiments of the present disclosure overcome such challenges. For example, referring now to FIG. 8, an example method 800 of generating combined drug input vectors and/or reduced drug input vectors in accordance with embodiments of the present disclosure is illustrated.

For example, the example method 800 may generate a plurality of drug input vectors associated with a drug identifier indicator, generate a combined drug input vector based at least in part on the plurality of drug input vectors, and optionally generate a plurality of reduced drug input vectors based at least in part on the plurality of combined drug input vectors. As such, the example method 800 may, for example but not limited to, programmatically generate predictions on multi-drug contraindications with improved accuracy.

Figure 8:
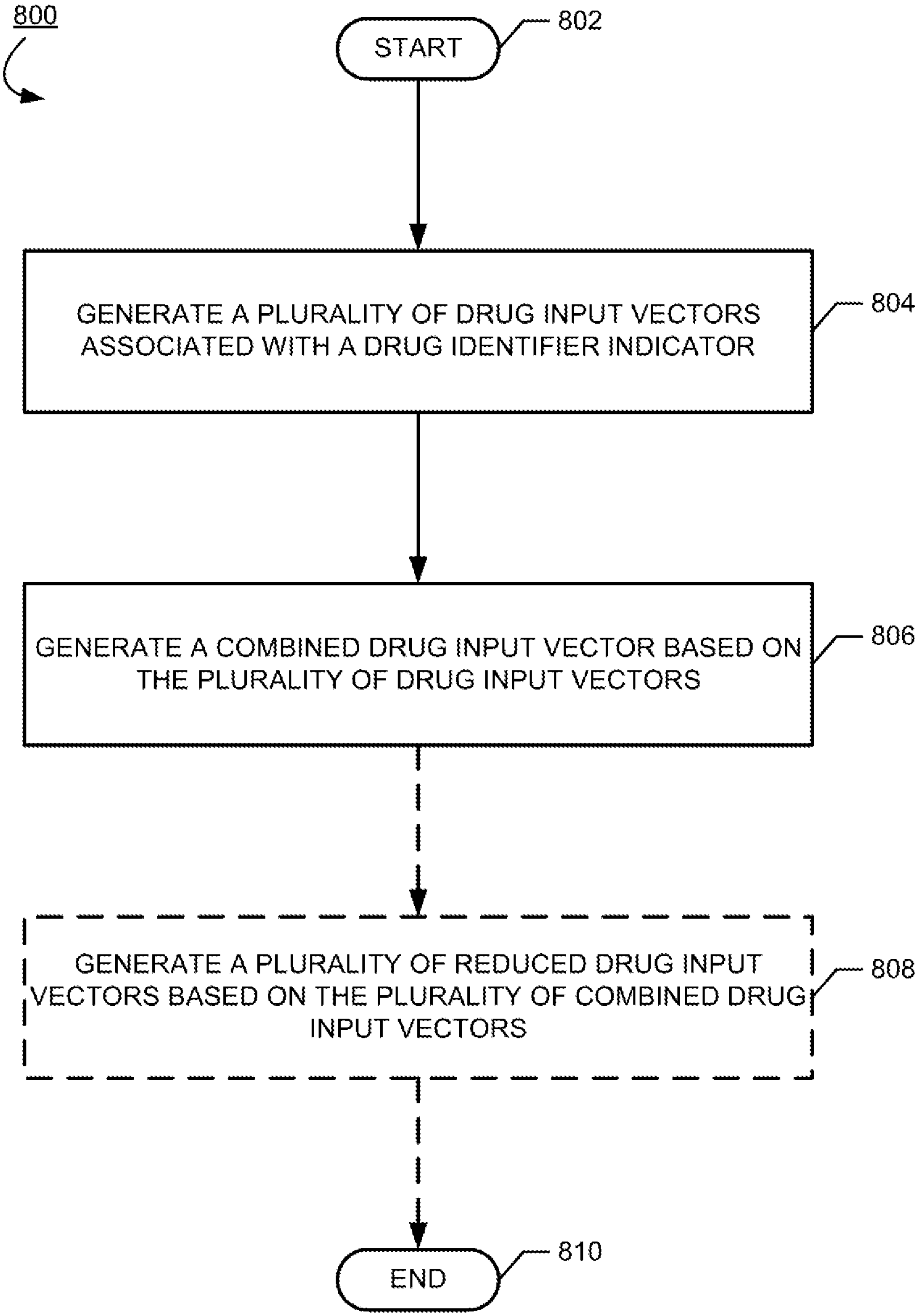

As shown in FIG. 8, the example method 800 starts at step/operation 802. Subsequent to and/or in response to step/operation 802, the example method 800 proceeds to step/operation 804. At step/operation 804, a computing entity includes means (such as the processing element 205 of the server computing entity 105 described above in connection with FIG. 1 and FIG. 2 and/or the processing element 308 of the client computing entity 101A described above in connection with FIG. 1 and FIG. 3) to generate a plurality of drug input vectors associated with a drug identifier indicator.

As described above, various embodiments of the present disclosure provide various types of drug input vectors that include, but are not limited to, drug text vectors, drug-gene interaction vectors, molecular structure vectors, drug-drug interaction vectors, drug-condition interaction vectors, and/or the like. In some embodiments, the plurality of drug input vectors comprises one or more of a drug text vector associated with the drug identifier indicator, a drug-gene interaction vector associated with the drug identifier indicator, a molecular structure vector associated with the drug identifier indicator, a drug-drug interaction vector associated with the drug identifier indicator, or a drug-condition interaction vector associated with the drug identifier indicator.

As an example, the computing entity may generate a drug text vector associated with Omeprazole. In such an example, the drug text vector comprises textual information of Omeprazole (including, but not limited to, one or more descriptions of Omeprazole, one or more summaries of Omeprazole, one or more medical facts associated with Omeprazole, and/or the like). Additionally, or alternatively, the computing entity may generate a drug-gene interaction vector associated with Omeprazole. In such an example, the drug-gene interaction vector indicates one or more known interactions between Omeprazole and genes. Additionally, or alternatively, the computing entity may generate a molecular structure vector associated with Omeprazole. In such an example, the molecular structure vector comprises a vector representation of an Omeprazole's structure of atoms and bonds between them. Additionally, or alternatively, the computing entity may generate a drug-drug interaction vector associated with Omeprazole. In such an example, the drug-drug interaction vector indicates known interactions between Omeprazole and other drugs. Additionally, or alternatively, the computing entity may generate a drug-condition interaction vector associated with Omeprazole. In such an example, the drug-condition interaction vector comprises known interactions between Omeprazole and health conditions.

While the description above provides an example of drug input vectors associated with Omeprazole, it is noted that the scope of the present disclosure is not limited to the description above. In some examples, various embodiments of the present disclosure may generate a plurality of drug input vectors associated with one or more additional or alternative drugs.

In some embodiments, the computing entity generates one or more drug input vectors for each of many drugs. In some embodiments, the more drugs that are considered, the more comprehensive that example embodiments of the present disclosure can detect contraindicated combinations. In some embodiments, the types of drug input vectors generated are consistent among the drugs considered.

While the descriptions above provide example types of drug input vectors, it is noted that the scope of the present disclosure is not limited to the example types above. In some examples, an example method generates less than the example types above. In some embodiments, an example method additionally or alternative generates types of drug input vectors other than the examples above.

As illustrated in the examples above, various embodiments of the present disclosure may provide technical benefits and advantages. For example, by incorporating biological elements of drugs into a predictive framework and providing biologically driven embeddings for constructing machine learning models, various embodiments of the present disclosure may improve the accuracy in predicting multi-drug contraindications.

Referring back to FIG. 8, subsequent to and/or in response to step/operation 804, the example method 800 proceeds to step/operation 806. At step/operation 806, a computing entity includes means (such as the processing element 205 of the server computing entity 105 described above in connection with FIG. 1 and FIG. 2 and/or the processing element 308 of the client computing entity 101A described above in connection with FIG. 1 and FIG. 3) to generate a combined drug input vector based at least in part on the plurality of drug input vectors.

As described above in connection with step/operation 804, example embodiments of the present disclosure may generate more than one type of drug input vector associated with each drug identifier indication. In some embodiments, the computing entity combines the plurality of drug input vectors associated with a drug identifier indicator into a signal combined drug input vector.

In some embodiments, the computing entity may append each drug input vector associated with the same drug identifier indicator one after another to generate the combined drug input vector. In some embodiments, the combined drug input vector is associated with the drug identifier indicator identified at step/operation 804 above.

Continuing from the Omeprazole example above, the computing entity may generate a combined drug input vector for Omeprazole by appending a drug text vector associated with Omeprazole after a drug-gene interaction vector associated with Omeprazole, appending a molecular structure vector associated with Omeprazole after the drug text vector associated with Omeprazole, appending a drug-drug interaction vector associated with Omeprazole after the molecular structure vector associated with Omeprazole, and appending a drug-condition interaction vector associated with Omeprazole after the drug-drug interaction vector associated with Omeprazole.

While the description above provides an example method of generating a combined drug input vector, it is noted that the scope of the present disclosure is not limited to the description above. In some examples, an example method may generate the combined drug input vector through other mechanisms.

Referring back to FIG. 8, subsequent to and/or in response to step/operation 806, the example method 800 optionally proceeds to step/operation 808. At step/operation 808, a computing entity includes means (such as the processing element 205 of the server computing entity 105 described above in connection with FIG. 1 and FIG. 2 and/or the processing element 308 of the client computing entity 101A described above in connection with FIG. 1 and FIG. 3) to generate a plurality of reduced drug input vectors based at least in part on the plurality of combined drug input vectors.

In some embodiments, the computing entity may generate reduced drug input vectors based at least in part on, for example, principal components analysis and auto-encoders on the plurality of combined drug input vectors generated at step/operation 806. In some embodiments, reduced drug input vectors have reduced vector lengths compared to the vector lengths of the combined drug vectors. In some embodiments, the reduced drug input vectors provide technical benefits and advantages such as, but not limited to, substantially reducing computational costs and increasing statistical power of the drug input vectors.

While the description above provides an example of generating a plurality of reduced drug input vectors, it is noted that the scope of the present disclosure is not limited to the description above. In some examples, an example method may generate reduced drug input vectors through other mechanisms. In some examples, an example method may forgo generating reduced drug input vectors.

Referring back to FIG. 8, subsequent to and/or in response to step/operation 808, the example method 800 proceeds to step/operation 810 and ends.

As described above, there are technical challenges, deficiencies and problems associated with generating computerized predictions on multi-drug contraindications, and various example embodiments of the present disclosure overcome such challenges. For example, referring now to FIG. 9, an example method 900 of generating dimensions associated with a multidimensional patient-drug tensor in accordance with embodiments of the present disclosure is illustrated. In some embodiments, each multidimensional patient-drug tensor comprises a patient identity dimension, a drugs taken dimension, and a drug representation dimension.

For example, the example method 900 may generate a patient identity dimension and a drugs taken dimension based at least in part on the plurality of patient record data objects, and may generate a drug representation dimension based at least in part on the plurality of combined drug input vectors. As such, the example method 900 may, for example but not limited to, programmatically generate predictions on multi-drug contraindications with improved accuracy.

Figure 9:
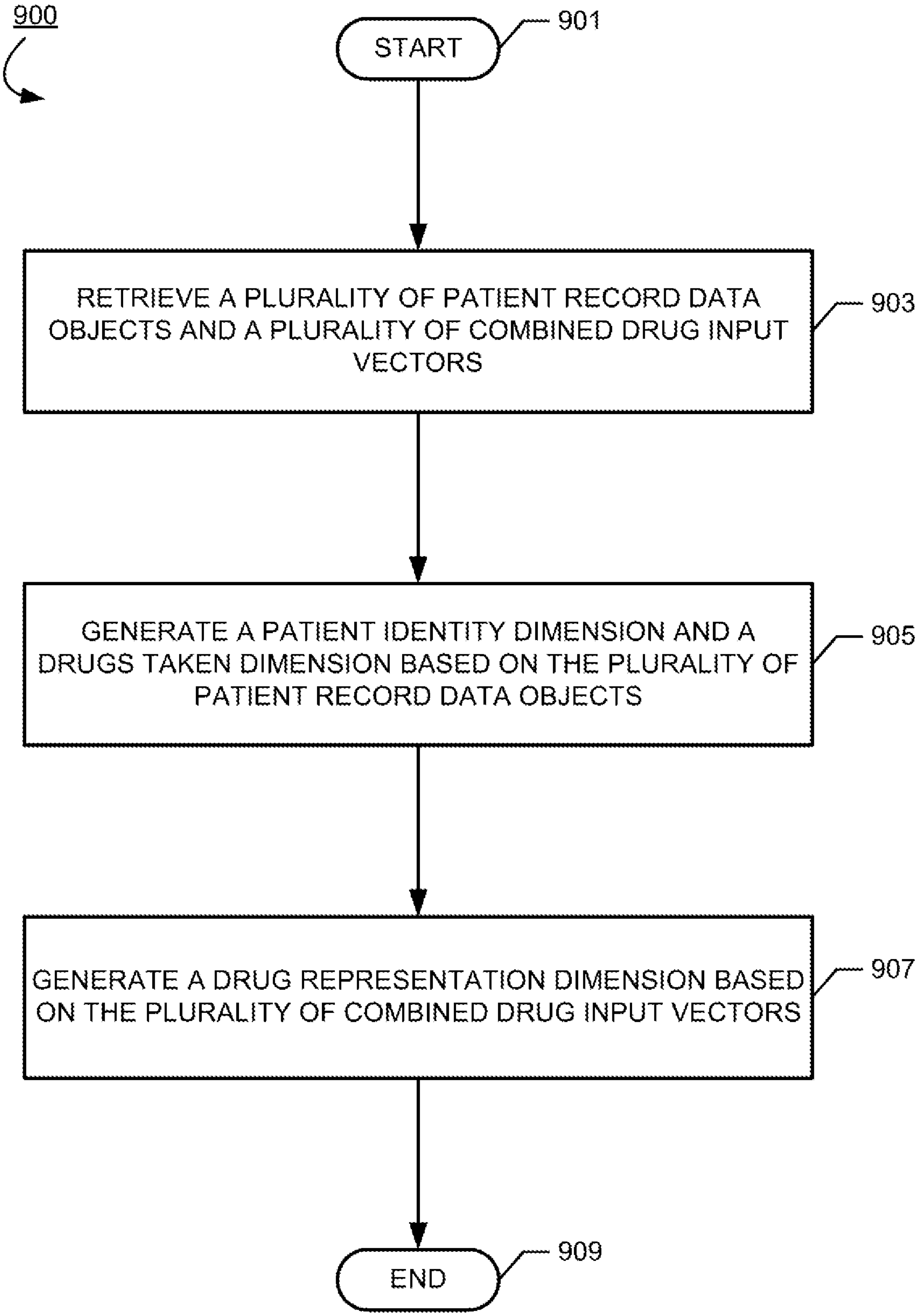

As shown in FIG. 9, the example method 900 starts at step/operation 901. Subsequent to and/or in response to step/operation 901, the example method 900 proceeds to step/operation 903. At step/operation 903, a computing entity includes means (such as the processing element 205 of the server computing entity 105 described above in connection with FIG. 1 and FIG. 2 and/or the processing element 308 of the client computing entity 101A described above in connection with FIG. 1 and FIG. 3) to retrieve a plurality of patient record data objects and a plurality of combined drug input vectors.

For example, the computing entity may retrieve the plurality of patient record data objects from a patient record data repository. In some embodiments, each of the plurality of patient record data objects comprises a patient identifier indicator, one or more drug identifier indicators associated with the patient identifier indicator, one or more health outcome indicators associated with the patient identifier indicator, and/or the like.

Referring back to FIG. 9, subsequent to and/or in response to step/operation 903, the example method 900 proceeds to step/operation 905. At step/operation 905, a computing entity includes means (such as the processing element 205 of the server computing entity 105 described above in connection with FIG. 1 and FIG. 2 and/or the processing element 308 of the client computing entity 101A described above in connection with FIG. 1 and FIG. 3) to generate a patient identity dimension and a drugs taken dimension of a multidimensional patient-drug tensor based at least in part on the plurality of patient record data objects.

In some embodiments, the computing entity generates the patient identity dimension of the multidimensional patient-drug tensor. For example, the computing entity generates the patient identity dimension based at least in part on incorporating the plurality of patient identifier indicators associated with the plurality of patient record data objects to the patient identity dimension, so that the patient identity dimension of the multidimensional patient-drug tensor comprises the plurality of patient identifier indicators.

In some embodiments, the computing entity further incorporates the plurality of health outcome indicators to the patient identity dimension. In such an example, each of the plurality of health outcome indicators is connected to one of the plurality of patient identifier indicators in the patient identity dimension described above, so that the patient identity dimension of the multidimensional patient-drug tensor comprises the plurality of health outcome indicators mapped or connected to the plurality of patient identifier indicators.

In some embodiments, the computing entity generates the drugs taken dimension of the multidimensional patient-drug tensor based at least in part on incorporating the drug identifier indicators associated with the patient record data objects. In some embodiments, each of the drug identifier indicators in the drugs taken dimension of the multidimensional patient-drug tensor is mapped or connected to one of the patient identifier indicators in the patient identity dimension based at least in part on the patient record data objects. In such embodiments, the multidimensional patient-drug tensor can indicate that one or more drugs (based at least in part on the drugs taken dimension) are taken by multiple users (based at least in part on the patient identity dimension).

Referring back to FIG. 9, subsequent to and/or in response to step/operation 905, the example method 900 proceeds to step/operation 907. At step/operation 907, a computing entity includes means (such as the processing element 205 of the server computing entity 105 described above in connection with FIG. 1 and FIG. 2 and/or the processing element 308 of the client computing entity 101A described above in connection with FIG. 1 and FIG. 3) to generate a drug representation dimension of the multidimensional patient-drug tensor based at least in part on the plurality of combined drug input vectors.

As described above in connection with at least FIG. 8, various embodiments of the present disclosure may generate a plurality of combined drug input vectors associated with a plurality of drug identifier indicators. In some embodiments, the computing entity generates the drug representation dimension of the multidimensional patient-drug tensor based at least in part on incorporating the combined drug input vectors to the drug representation dimension.

For example, as described above, the computing entity may generate the drugs taken dimension of the multidimensional patient-drug tensor based at least in part on a plurality of drug identifier indicators associated with the plurality of patient record data objects. In some embodiments, the computing entity generates a combined drug input vector for each of the plurality of drug identifier indicators, and adds the combined drug input vector to the drug representation dimension. In some embodiments, the computing entity maps or connects each of the combined drug input vectors in the drug representation dimension to one of the drug identifier indicators in the drugs taken dimension.

Referring back to FIG. 9, subsequent to and/or in response to step/operation 907, the example method 900 proceeds to step/operation 909 and ends.

e. Exemplary Techniques for Generating Interaction Attentive Prediction Data Objects As described above, there are technical challenges, deficiencies and problems associated with generating computerized predictions on multi-drug contraindications, and various example embodiments of the present disclosure overcome such challenges. For example, referring now to FIG. 10, an example method 1000 of generating interaction-attentive prediction data objects in accordance with embodiments of the present disclosure is illustrated.

For example, the example method 1000 may generate a plurality of encoded multidimensional tensors based at least in part on inputting a plurality of multidimensional patient-drug tensors to an interaction-attentive encoding machine learning model, and generate an interaction-attentive prediction data object based at least in part on inputting the plurality of encoded multidimensional tensors to an interaction-attentive predicting machine learning model. As such, the example method 1000 may, for example but not limited to, programmatically generate predictions on multi-drug contraindications with improved accuracy.

Figure 10:
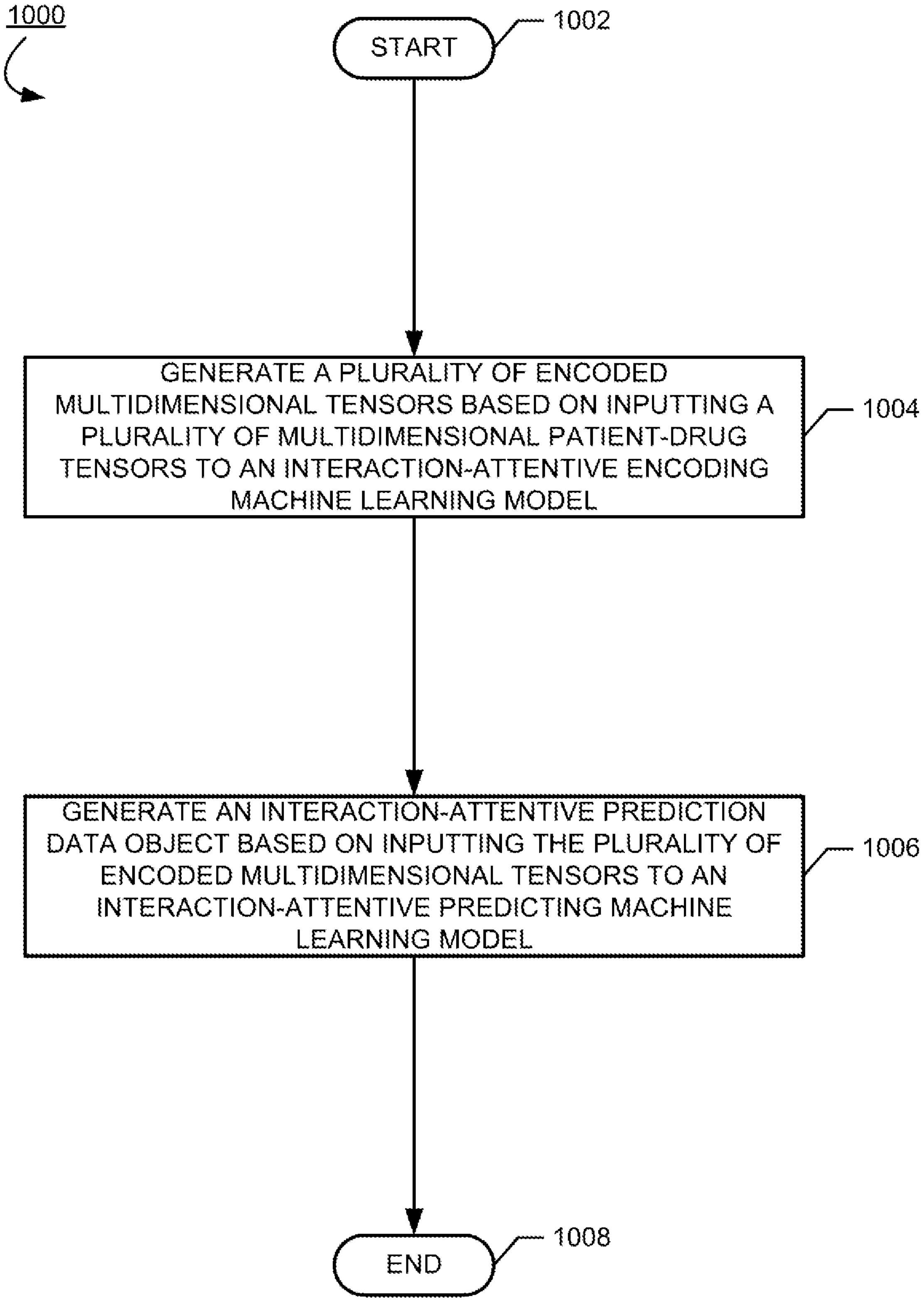

As shown in FIG. 10, the example method 1000 starts at step/operation 1002. Subsequent to and/or in response to step/operation 1002, the example method 1000 proceeds to step/operation 1004. At step/operation 1004, a computing entity includes means (such as the processing element 205 of the server computing entity 105 described above in connection with FIG. 1 and FIG. 2 and/or the processing element 308 of the client computing entity 101A described above in connection with FIG. 1 and FIG. 3) to generate a plurality of encoded multidimensional tensors based at least in part on inputting a plurality of multidimensional patient-drug tensors to an interaction-attentive encoding machine learning model.

As described above, the interaction-attentive encoding machine learning model is a type of interaction-attentive machine learning model that encodes multidimensional tensors such as, but not limited to, a plurality of multidimensional patient-drug tensors (such as, but not limited to, multidimensional patient-drug tensors generated in accordance with FIG. 6A, FIG. 6B, and/or FIG. 9).

In some embodiments, the interaction-attentive encoding machine learning model comprises a multi-head attention encoder. In such embodiments, the computing entity applies the multi-head attention encoder to the plurality of multidimensional patient-drug tensors. In some embodiments, the multi-head attention encoder uses three matrices to measure an attention score between any pair of drug identifier indicators in the multidimensional patient-drug tensors, and generate an attention relationship indicator based at least in part on the attention score.

In some embodiments, the multi-head attention encoder represents the embedding of each drug as a combination of its co-prescribed drugs, weighted based at least in part on the calculated attention score. In some embodiments, to emphasize drug interactions, the computing entity adjusts the multi-head attention encoder to remove the possibility that a drug has attention to itself. In some embodiments, the output of the multi-head attention encoder is an encoded multidimensional tensor of the same dimensions as the multidimensional patient-drug tensor that is provided to the multi-head attention encoder as an input. In some embodiments, the encoded multidimensional tensor generated by the multi-head attention encoder contains information about attention relationships between drugs. For example, multidimensional tensors that are encoded by the interaction-attentive encoding machine learning model comprises attention relationship indicators associated with the plurality of drug identifier indicators in the multidimensional patient-drug tensors.

In some embodiments, the computing entity may modify the multi-head attention encoder to improve encoding results by, for example but not limited to, altering loss functions, hyperparameters, and attention metrics. For example, during training of the multi-head attention encoder, the computing entity may cause slight decreases to the loss function associated with the multi-head attention encoder if the multi-head attention encoder has large attention to multiple drugs (for example, but not limited to, using a function such as a Gini inequality metric). In some embodiments, the computing entity determines the adjustment to the loss function based at least in part on, for example, implementing a hyperparameter that decays across the multi-head attention encoder training. Additionally, or alternatively, the computing entity may further reduce the attention metrics falling below a threshold (e.g., to zero) to further accentuate the impact of the remaining set of drug combinations. In some embodiments, the computing entity may modify the multi-head attention encoder so that it is more sensitive to interaction between groups of three ("triplets"), four ("quadruplets"), or more drugs.

Figure 11:
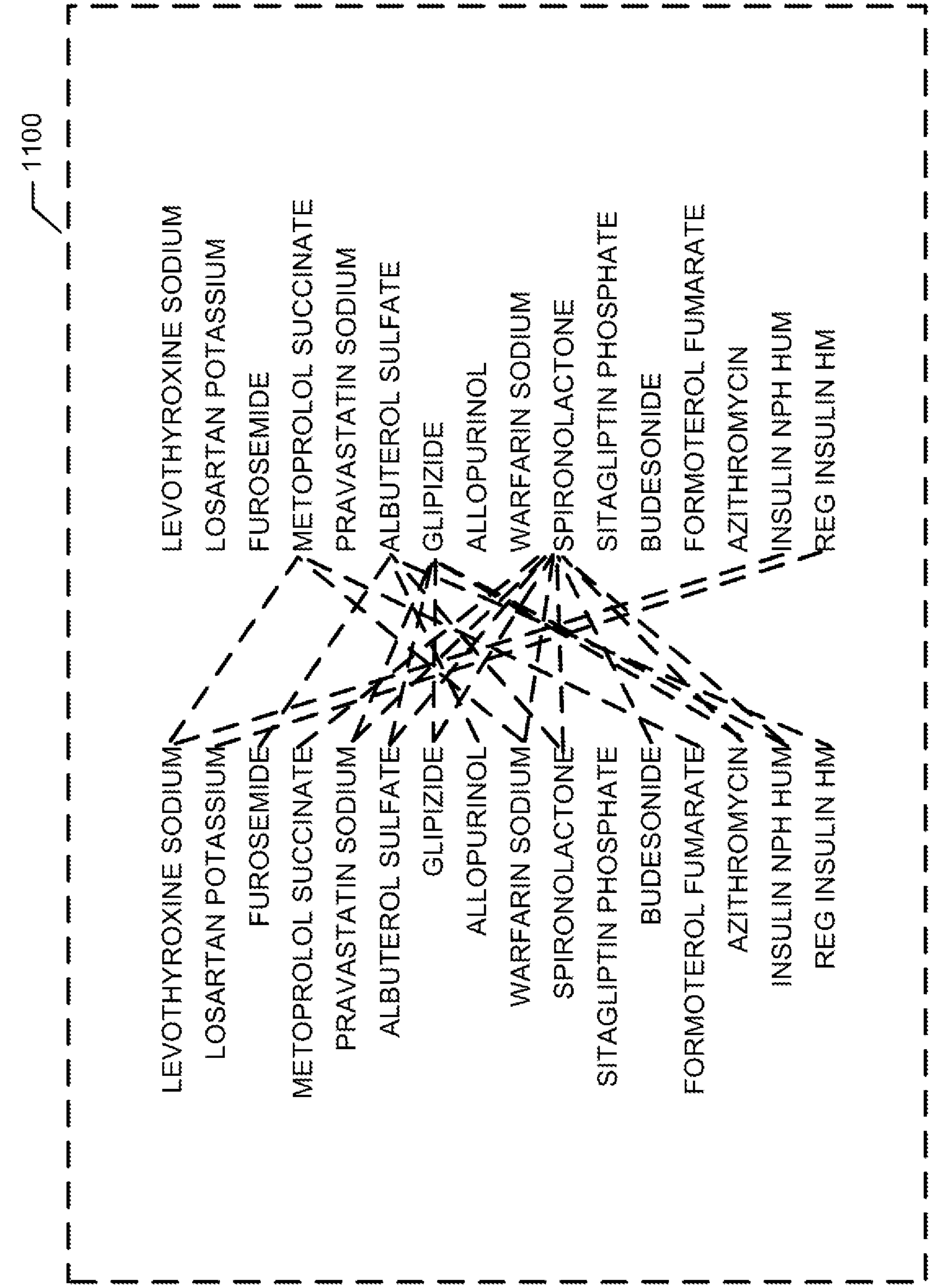

Referring now to FIG. 11, an example graphic representation 1100 of an example multi-head attention encoder in accordance with some embodiments of the present disclosure is illustrated. In particular, the example graphic representation 1100 shows example attentions from one head of the example multi-head attention encoder.

As illustrated in the example shown in FIG. 11, an example multi-head attention encoder in accordance with some embodiments of the present disclosure incorporates transformer structures so that a machine learning model (for example, an interaction-attentive predicting machine learning model described herein) can be driven to identify drug interactions based at least in part on the attentions from the encoded multidimensional tensors. In some embodiments, an example multi-head attention encoder may provide sequential transformers so that complex interactions can be captured.

While the description above provides an example multi-head attention encoder as an interaction-attentive encoding machine learning model, it is noted that the scope of the present disclosure is not limited to the description above. In some examples, an example interaction-attentive encoding machine learning model may comprise one or more additional and/or alternative models such as, but not limited to, a single-headed attention encoder, a feed-forward neural network, a nearest neighbor model, and/or the like. In some examples, one or more interaction-attentive encoding machine learning models in accordance with some embodiments of the present disclosure can be associated with other model types that account for co-occurrence of drugs, such as, but not limited to, decision tree, random forest, polynomial regression, and/or the like.

Referring back to FIG. 10, subsequent to and/or in response to step/operation 1004, the example method 1000 proceeds to step/operation 1006. At step/operation 1006, a computing entity includes means (such as the processing element 205 of the server computing entity 105 described above in connection with FIG. 1 and FIG. 2 and/or the processing element 308 of the client computing entity 101A described above in connection with FIG. 1 and FIG. 3) to generate an interaction-attentive prediction data object based at least in part on inputting the plurality of encoded multidimensional tensors to an interaction-attentive predicting machine learning model.

In some embodiments, the interaction-attentive predicting machine learning model comprises a feed-forward neural network. In some embodiments, the feed-forward neural network comprises a plurality of neural network layers. In some embodiments, the computing entity applies a feed-forward neural network to the plurality of encoded multidimensional tensors generated in connection with step/operation 1004.

Figure 12:
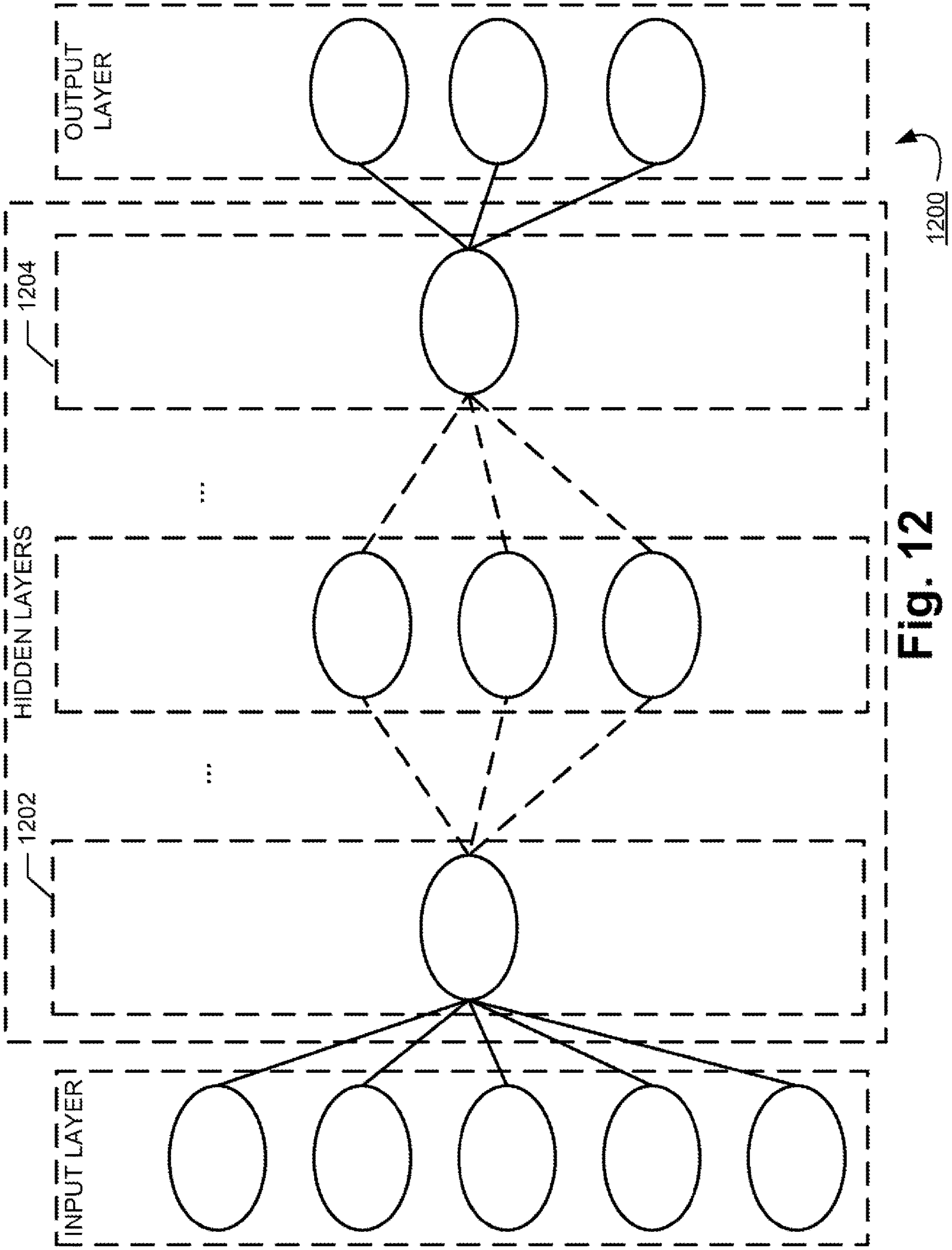

Referring now to FIG. 12, an example feed-forward neural network 1200 is shown. In some embodiments, the feed-forward neural network 1200 comprises an interconnected group of nodes, and each node represents a mathematical function. In some embodiments, the input to each node may include a set of input values and associated weights, and the mathematical function of the node may map the inputs and weights to an output. In some embodiments, the arrows connecting the nodes represent connections from the output of one node to the input of another node.

In some embodiments, nodes are aggregated into layers, and different layers may perform different transformations of their corresponding inputs. In the example shown in FIG. 12, the example feed-forward neural network 1200 includes at least three layers: an input layer, one or more hidden layer(s), and an output layer.

In some embodiments, the input layer of the example feed-forward neural network 1200 reduces the dimensionality of encoded multidimensional tensors to two dimensions (for example, in the form of a matrix comprising rows and columns described above). In some embodiments, the output from the output layer of the feed-forward neural network 1200 is a two-dimensional matrix with a number of rows corresponding to the number of patients associated with the encoded multidimensional tensors and at least one of two columns. In some embodiments, at least one column corresponds to interaction-attentive predicted outcome indicators that are outputs from a SoftMax layer and correspond to either the probability of a predicted favorable health outcome or the probability of a predicted unfavorable health outcome. In some embodiments, the predicted favorability of an outcome is determined based at least in part on one or more interactions between one or more drugs associated with the encoded multidimensional tensors.

While the description above provides an example interaction-attentive predicted outcome indicator in the form of binary favorable/unfavorable health outcome, it is noted that the scope of the present disclosure is not limited to the description above. For example, the example interaction-attentive predicted outcome indicator can be a continuous output (such as, but not limited to, predicting a scalar lab result). In such an example, the computing entity chains the SoftMax layer activation to an alternative.

In some embodiments, the example feed-forward neural network 1200 may comprise different numbers of layers and different node counts in each layer depending on the types of patient-specific information available to customize the prediction of harmful drug combinations.

In some embodiments, if demographic information is available for the patients in the training data set for the example feed-forward neural network 1200, predictive value of the demographic variables can be introduced by adding layers to the example feed-forward neural network 1200 in which each layer corresponds to a demographic variable.

For example, the plurality of patient record data objects comprises a plurality of patient gender indicators indicating biological genders associated with the patients. In such examples, information on biological genders could be introduced into the example feed-forward neural network 1200 by adding a layer of a single node representing gender as a binary value. In the example shown in FIG. 12, the plurality of neural network layers of the example feed-forward neural network 1200 comprises a patient gender layer 1202 as one of the hidden layers.

Additionally, or alternatively, the plurality of patient record data objects comprises a plurality of patient age indicators. In such examples, data on patient age could be added to the example feed-forward neural network 1200 as another layer with a single node. In the example shown in FIG. 12, the plurality of neural network layers comprises a patient age layer 1204 as one of the hidden layers in the example feed-forward neural network 1200.

While the description above provides an example of a feed-forward neural network as an interaction-attentive predicting machine learning model, it is noted that the scope of the present disclosure is not limited to the description above. In some examples, an example interaction-attentive predicting machine learning model may comprise one or more additional and/or alternative models. For example, an example interaction-attentive predicting machine learning model can incorporate one-hot encoded variables or embeddings that represent a patient's baseline health conditions (based at least in part on the health condition indicators from the patient record data objects) as a method to account for potential confounders. In some embodiments, to improve one-hot encodings, the computing entity may generate covariance matrices to represent baseline conditions to capture common comorbidities. Additionally, or alternative, the interaction-attentive encoding machine learning model comprises one or more machine learning models associated with other model types that account for co-occurrence of drugs, such as, but not limited to, decision tree, random forest, polynomial regression, and/or the like.

Referring back to FIG. 10, subsequent to and/or in response to step/operation 1006, the example method 1000 proceeds to step/operation 1008 and ends.

As illustrated various examples above, example embodiments of the present disclosure utilize biologically driven embeddings and interaction-attentive encoding machine learning models (such as, but not limited to, multi-head attention encoders). For example, various embodiments of the present disclosure combine a transformer framework (for example, but not limited to, a multi-head attention encoder) with various dimensions of multidimensional patient-drug tensors (for example, but not limited to, long-term laboratory results and pharmacy claims from the patient identify dimension) to generate interaction-attentive prediction data objects that provide predictions, estimates, and forecasts on higher-order drug interactions.

f. Exemplary Techniques for Generating Interaction-Inattentive Prediction Data Object As described above, there are technical challenges, deficiencies and problems associated with generating computerized predictions on multi-drug contraindications, and various example embodiments of the present disclosure overcome such challenges. For example, referring now to FIG. 13, an example method 1300 of generating an interaction-inattentive prediction data object in accordance with embodiments of the present disclosure is illustrated.

For example, the example method 1300 may retrieve a plurality of training patient record data objects comprising a plurality of patient condition indicators and a plurality of health outcome indicators, generate an interaction-inattentive machine learning model based at least in part on the plurality of training patient record data objects, and generate an interaction-inattentive prediction data object based at least in part on inputting the plurality of patient record data objects to the interaction-inattentive machine learning model. As such, the example method 1300 may, for example but not limited to, programmatically generate predictions on multi-drug contraindications with improved accuracy.

Figure 13:
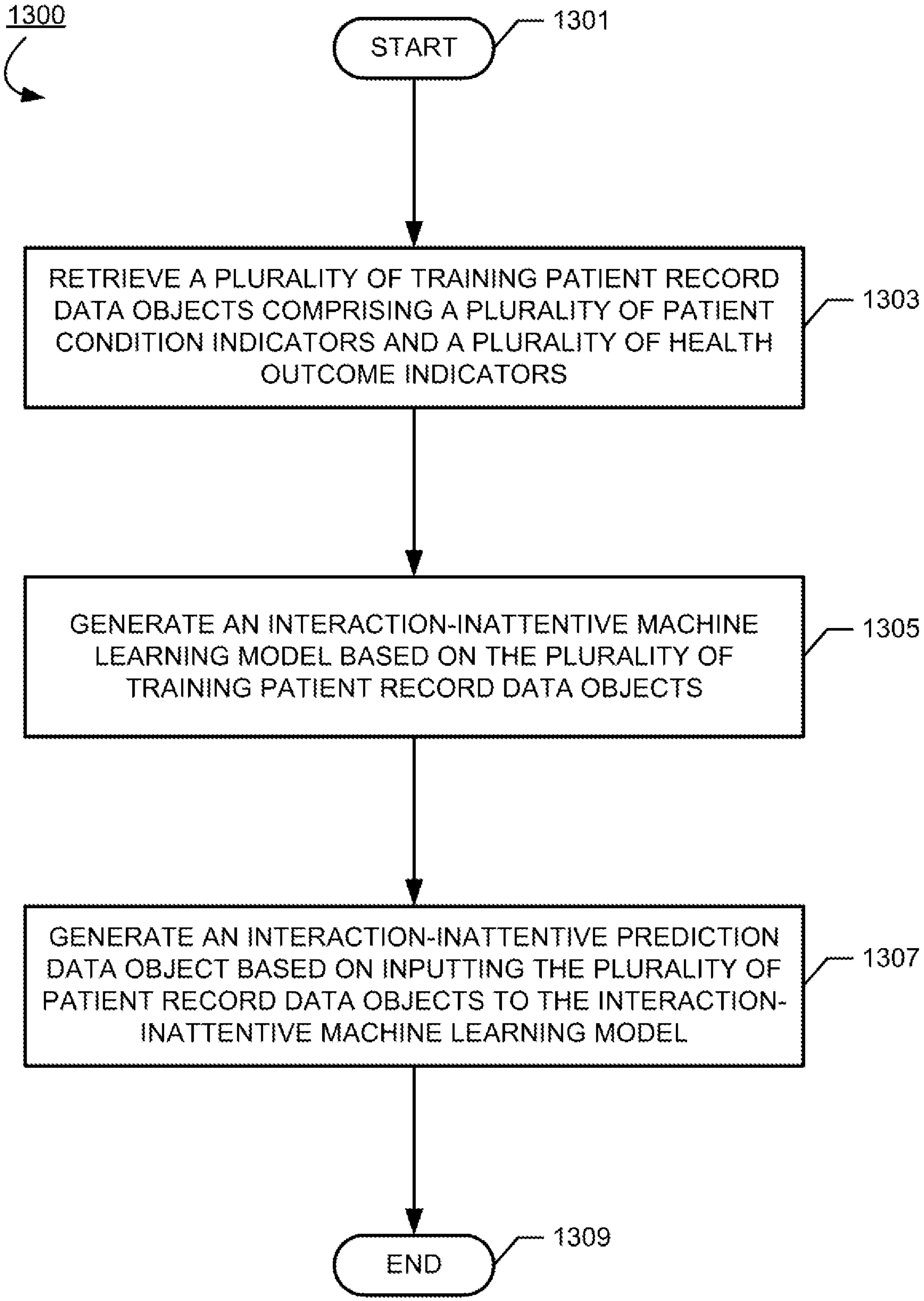

As shown in FIG. 13, the example method 1300 starts at step/operation 1301. Subsequent to and/or in response to step/operation 1301, the example method 1300 proceeds to step/operation 1303. At step/operation 1303, a computing entity includes means (such as the processing element 205 of the server computing entity 105 described above in connection with FIG. 1 and FIG. 2 and/or the processing element 308 of the client computing entity 101A described above in connection with FIG. 1 and FIG. 3) to retrieve a plurality of training patient record data objects comprising a plurality of patient condition indicators and a plurality of health outcome indicators.

As described above, training patient record data objects may refer to a type of patient record data object that is used for training one or more machine learning models. In some embodiments, the computing entity retrieves the plurality of training patient record data objects from a training patient record data object repository.

In some embodiments, each of the plurality of training patient record data objects comprises one or more patient condition indicators and one or more health outcome indicators. In some embodiments, each of the one or more patient condition indicators represents, indicates, stores and/or comprises one or more indications associated with one or more known health conditions of the patient. In some embodiments, each of the one or more health outcome indicators represents, indicates, stores and/or comprises one or more known health levels/outcomes associated with one or more users, including, but not limited to, a long-term health level/outcome of the user, a short-term health level/outcome of the user, and/or the like.

Referring back to FIG. 13, subsequent to and/or in response to step/operation 1303, the example method 1300 proceeds to step/operation 1305. At step/operation 1305, a computing entity includes means (such as the processing element 205 of the server computing entity 105 described above in connection with FIG. 1 and FIG. 2 and/or the processing element 308 of the client computing entity 101A described above in connection with FIG. 1 and FIG. 3) to generate an interaction-inattentive machine learning model based at least in part on the plurality of training patient record data objects.

In some embodiments, the computing entity generates the interaction-inattentive machine learning model based at least in part on training the interaction-inattentive machine learning model using the training patient record data objects.

In some embodiments, the interaction-inattentive machine learning model comprises a logistic regression model. In some embodiments, the logistic regression model is a type of supervised machine learning model that can be trained by adjusting the parameters or weights of the logistic regression model. For example, the computing entity provides the patient condition indicators of the plurality of training patient record data objects as inputs for training the logistic regression model. In such examples, the computing entity causes the logistic regression model to adjust its parameters and/or weights so that the logistic regression model generates interaction-inattentive predicted outcome indicators that match the health outcome indicators from the training patient record data objects. For example, the logistic regression model can be trained to generate interaction-inattentive predicted outcome indicators predicting patient health outcome (i.e., favorable/positive, or unfavorable/negative) using the one-hot encoded variables or embeddings that represent a patient's baseline health conditions described above.

While the description above provides an example logistic regression model as an interaction-inattentive machine learning model, it is noted that the scope of the present disclosure is not limited to the description above. In some examples, an example interaction-inattentive machine learning model may comprise one or more additional and/or alternative models.

Referring back to FIG. 13, subsequent to and/or in response to step/operation 1305, the example method 1300 proceeds to step/operation 1307. At step/operation 1307, a computing entity includes means (such as the processing element 205 of the server computing entity 105 described above in connection with FIG. 1 and FIG. 2 and/or the processing element 308 of the client computing entity 101A described above in connection with FIG. 1 and FIG. 3) to generate an interaction-inattentive prediction data object based at least in part on inputting the plurality of patient record data objects to the interaction-inattentive machine learning model.

As described above in connection with step/operation 1305, the computing entity may generate a logistic regression model as an interaction-inattentive machine learning model in accordance with some embodiments of the present disclosure. In some embodiments, the computing entity applies the logistic regression model to each patient record data object in the patient record data object to generate the interaction-inattentive prediction data object.

In some embodiments, the computing entity may apply a series of logistic regression models on the plurality of patient record data objects to generate the interaction-inattentive prediction data object. In some embodiments, similar to the interaction-attentive prediction data objects described above, the interaction-inattentive prediction data object is a two-dimensional matrix with a number of rows that equals the number of patients associated with the patient record data objects and at least one of two columns. In some embodiments, at least one column corresponds to interaction-inattentive predicted outcome indicators corresponding to either the probability of a predicted favorable health outcome or the probability of a predicted unfavorable health outcome. In some embodiments, the predicted favorability of an outcome is determined based at least in part on the health outcome indicator associated with the plurality of patient record data objects (for example, increases in creatinine measurements as described above).

As illustrated in the example above, example embodiments of the present disclosure provide a baseline linear model that incorporates each feature from the patient record data object as one-hot encodings. As the baseline linear model does not analyze interactions between drugs, the interaction-inattentive prediction data object generated by the baseline linear model are not based at least in part on interactions between drugs.

While the description above provides an example logistic regression model as an interaction-inattentive machine learning model, it is noted that the scope of the present disclosure is not limited to the description above. In some examples, an example interaction-inattentive machine learning model may comprise one or more additional and/or alternative models.

Referring back to FIG. 13, subsequent to and/or in response to step/operation 1307, the example method 1300 proceeds to step/operation 1309 and ends.

V. CONCLUSION

Many modifications and other embodiments of the disclosure set forth herein will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A system comprising:

one or more processors; and one or more memories storing processor-executable instructions that, when executed by the one or more processors, cause the one or more processors to perform operations comprising:

generating a plurality of reduced drug input vectors based at least in part on a plurality of combined drug input vectors, wherein a combined drug input vector of the plurality of combined drug input vectors corresponds to a first drug and a second drug;

inputting a plurality of record data objects and the plurality of reduced drug input vectors to an encoding layer of an interaction-attentive machine learning model to receive a plurality of encoded multidimensional tensors;

inputting the plurality of encoded multidimensional tensors to a transformer layer of the interaction-attentive machine learning model to receive an interaction-attentive prediction data object, wherein the interaction-attentive prediction data object describes a predicted interaction between the first drug and the second drug;

inputting the plurality of record data objects to an interaction-inattentive machine learning model to receive an interaction-inattentive prediction data object, wherein the interaction-inattentive machine learning model comprises a logistic regression model that is trained to determine a predicted outcome based at least in part on the plurality of record data objects; and training the interaction-attentive machine learning model based at least in part on a predicted significance indicator corresponding to a combination indicator that indicates a likelihood that a defined outcome is associated with a combination of one or more of the plurality of combined drug input vectors, wherein the likelihood is determined based at least in part on a comparison of the interaction-attentive prediction data object and the interaction-inattentive prediction data object.

2. The system of claim 1, wherein the processor-executable instructions further cause the one or more processors to:

generate a plurality of input vectors associated with an identifier indicator; and generate a first combined drug input vector, among the plurality of combined drug input vectors, based at least in part on the plurality of input vectors, wherein the first combined drug input vector is associated with the identifier indicator.

3. The system of claim 2, wherein the plurality of input vectors comprises one or more of a text vector associated with the identifier indicator, an interaction vector associated with the identifier indicator, a structure vector associated with the identifier indicator, a drug-drug interaction vector associated with the identifier indicator, or a drug-condition interaction vector associated with the identifier indicator.

4. The system of claim 1, wherein one or more of the plurality of encoded multidimensional tensors comprises a patient identity dimension, a drugs taken dimension, and a representation dimension, wherein the processor-executable instructions further cause the one or more processors to:

generate the patient identity dimension and the drugs taken dimension based at least in part on the plurality of record data objects; and generate the representation dimension based at least in part on the plurality of combined drug input vectors.

5. The system of claim 1, wherein the processor-executable instructions further cause the one or more processors to:

retrieve a plurality of training record data objects comprising a plurality of condition indicators and a plurality of outcome indicators; and generate the interaction-inattentive machine learning model based at least in part on the plurality of training record data objects.

6. The system of claim 1, wherein the processor-executable instructions further cause the one or more processors to:

determine at least one identifier indicator that is associated with:

(1) an interaction-attentive predicted outcome indicator, from the interaction-attentive prediction data object, indicating a predicted unfavorable outcome, and (2) an interaction-inattentive predicted outcome indicator, from the interaction-inattentive prediction data object, indicating a predicted favorable outcome; and determine the combination indicator associated with the at least one identifier indicator based at least in part on the plurality of record data objects.

7. A computer-implemented method for generating predicted contraindication data objects comprising:

generating, by one or more processors, a plurality of reduced drug input vectors based at least in part on a plurality of combined drug input vectors, wherein a combined drug input vector of the plurality of combined drug input vectors corresponds to a first drug and a second drug;

inputting, by the one or more processors, a plurality of record data objects and the plurality of reduced drug input vectors to an encoding layer of an interaction-attentive machine learning model to receive a plurality of encoded multidimensional tensors;

inputting, by the one or more processors, the plurality of encoded multidimensional tensors to the interaction-attentive machine learning model to receive an interaction-attentive prediction data object, wherein the interaction-attentive prediction data object describes a predicted interaction between the first drug and the second drug;

inputting, by the one or more processors, the plurality of record data objects to an interaction-inattentive machine learning model to receive an interaction-inattentive prediction data object, wherein the interaction-inattentive machine learning model comprises a logistic regression model that is trained to determine a predicted outcome based at least in part on the plurality of record data objects; and training, by the one or more processors, the interaction-attentive machine learning model based at least in part on a predicted significance indicator corresponding to a combination indicator that indicates a likelihood that a defined outcome is associated with a combination of one or more of the plurality of combined drug input vectors, wherein the likelihood is determined based at least in part on a comparison of the interaction-attentive prediction data object and the interaction-inattentive prediction data object.

8. The computer-implemented method of claim 7, wherein the computer-implemented method further comprises:

generating, by the one or more processors, a plurality of input vectors associated with an identifier indicator; and generating, by the one or more processors, a first combined drug input vector, among the plurality of combined drug input vectors, based at least in part on the plurality of input vectors, wherein the first combined drug input vector is associated with the identifier indicator.

9. The computer-implemented method of claim 8, wherein the plurality of input vectors comprises one or more of a text vector associated with the identifier indicator, an interaction vector associated with the identifier indicator, a structure vector associated with the identifier indicator, a drug-drug interaction vector associated with the identifier indicator, or a drug-condition interaction vector associated with the identifier indicator.

10. The computer-implemented method of claim 7, wherein one or more of the plurality of encoded multidimensional tensors comprises a patient identity dimension, a drugs taken dimension, and a representation dimension, wherein the computer-implemented method further comprises:

generating, by the one or more processors, the patient identity dimension and the drugs taken dimension based at least in part on the plurality of record data objects; and generating, by the one or more processors, the representation dimension based at least in part on the plurality of combined drug input vectors.

11. The computer-implemented method of claim 7, wherein the computer-implemented method further comprises:

retrieving, by the one or more processors, a plurality of training record data objects comprising a plurality of condition indicators and a plurality of outcome indicators; and generating, by the one or more processors, the interaction-inattentive machine learning model based at least in part on the plurality of training record data objects.

12. The computer-implemented method of claim 7, further comprising:

determining, by the one or more processors, at least one identifier indicator that is associated with:

(1) an interaction-attentive predicted outcome indicator, from the interaction-attentive prediction data object, indicating a predicted unfavorable outcome, and (2) an interaction-inattentive predicted outcome indicator, from the interaction-inattentive prediction data object, indicating a predicted favorable outcome; and determining, by the one or more processors, the combination indicator associated with the at least one identifier indicator based at least in part on the plurality of record data objects.

13. One or more non-transitory computer-readable storage media including instructions that, when executed by one or more processors, cause the one or more processors to perform operations comprising:

generating a plurality of reduced drug input vectors based at least in part on a plurality of combined drug input vectors, wherein a combined drug input vector of the plurality of combined drug input vectors corresponds to a first drug and a second drug;

inputting a plurality of record data objects and the plurality of reduced drug input vectors to an encoding layer of an interaction-attentive machine learning model to receive a plurality of encoded multidimensional tensors;

inputting the plurality of encoded multidimensional tensors to a transformer layer of the interaction-attentive machine learning model to receive an interaction-attentive prediction data object, wherein the interaction-attentive prediction data object describes a predicted interaction between the first drug and the second drug;

inputting the plurality of record data objects to an interaction-inattentive machine learning model to receive an interaction-inattentive prediction data object, wherein the interaction-inattentive machine learning model comprises a logistic regression model that is trained to determine a predicted outcome based at least in part on the plurality of record data objects; and training the interaction-attentive machine learning model based at least in part on a predicted significance indicator corresponding to a combination indicator that indicates a likelihood that a defined outcome is associated with a combination of one or more of the plurality of combined drug input vectors, wherein the likelihood is determined based at least in part on a comparison of the interaction-attentive prediction data object and the interaction-inattentive prediction data object.

14. The one or more non-transitory computer-readable storage media of claim 13, wherein the instructions further cause the one or more processors to:

generate a plurality of input vectors associated with an identifier indicator; and generate a first combined drug input vector, among the plurality of combined drug input vectors, based at least in part on the plurality of input vectors, wherein the first combined drug input vector is associated with the identifier indicator.

15. The one or more non-transitory computer-readable storage media of claim 14, wherein the plurality of input vectors comprises one or more of a text vector associated with the identifier indicator, an interaction vector associated with the identifier indicator, a structure vector associated with the identifier indicator, a drug-drug interaction vector associated with the identifier indicator, or a drug-condition interaction vector associated with the identifier indicator.

16. The one or more non-transitory computer-readable storage media of claim 13, wherein one or more of the plurality of encoded multidimensional tensors comprises a patient identity dimension, a drugs taken dimension, and a representation dimension, and wherein the instructions further cause the one or more processors to:

generate the patient identity dimension and the drugs taken dimension based at least in part on the plurality of record data objects; and generate the representation dimension based at least in part on the plurality of combined drug input vectors.

17. The one or more non-transitory computer-readable storage media of claim 13, wherein the instructions further cause the one or more processors to:

retrieve a plurality of training record data objects comprising a plurality of condition indicators and a plurality of outcome indicators; and generate the interaction-inattentive machine learning model based at least in part on the plurality of training record data objects.

* * * * *